(12) United States Patent
Brown et al.

(10) Patent No.: US 11,208,396 B2
(45) Date of Patent: Dec. 28, 2021

(54) OXIME COMPOUNDS AS AGONISTS OF THE MUSCARINIC M1 AND/OR M4 RECEPTOR

(71) Applicant: Heptares Therapeutics Limited, Cambridge (GB)

(72) Inventors: Giles Albert Brown, Cambridge (GB); Benjamin Gerald Tehan, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 475 days.

(21) Appl. No.: 15/772,785

(22) PCT Filed: Nov. 2, 2016

(86) PCT No.: PCT/GB2016/053396
§ 371 (c)(1),
(2) Date: May 1, 2018

(87) PCT Pub. No.: WO2017/077292
PCT Pub. Date: May 11, 2017

(65) Prior Publication Data
US 2020/0165220 A1    May 28, 2020

(30) Foreign Application Priority Data
Nov. 2, 2015  (GB) ...................... 1519352

(51) Int. Cl.
| | | |
|---|---|---|
| *C07D 401/04* | (2006.01) | |
| *A61P 25/28* | (2006.01) | |
| *A61P 25/04* | (2006.01) | |
| *A61P 25/18* | (2006.01) | |
| *A61P 43/00* | (2006.01) | |
| *A61P 25/30* | (2006.01) | |
| *A61P 25/00* | (2006.01) | |

(52) U.S. Cl.
CPC ............ *C07D 401/04* (2013.01); *A61P 25/00* (2018.01); *A61P 25/04* (2018.01); *A61P 25/28* (2018.01); *A61P 25/30* (2018.01); *A61P 43/00* (2018.01); *A61P 25/18* (2018.01)

(58) Field of Classification Search
CPC ........ C07D 401/04; A61P 43/00; A61P 25/00; A61P 25/04; A61P 25/18; A61P 25/28; A61P 25/30
See application file for complete search history.

(56) References Cited

U.S. PATENT DOCUMENTS 7,067,507 B2 * 6/2006 Pulley .................... A61P 43/00
514/183

FOREIGN PATENT DOCUMENTS

| WO | 2000/66141 A2 | 11/2000 |
|---|---|---|
| WO | 2000066559 A1 | 11/2000 |
| WO | 2005/077369 A1 | 8/2005 |
| WO | 2013/072705 A1 | 5/2013 |
| WO | 2014/045031 A1 | 3/2014 |
| WO | 2014/122474 A1 | 8/2014 |
| WO | 2015/118342 A1 | 8/2015 |

OTHER PUBLICATIONS

Foster. Neuropsychiatric Disease and Treatment, 2014, 10, 183-191 (Year: 2014).*
Scarr. CNS Neuroscience and Therapeutics, 2012, 18, 369-379 (Year: 2012).*
Martino. Pain, 2011, 152, 2852-60 (Year: 2011).*
Katz. Expert Reviews, 2009, 9:5, 723-744 (Year: 2009).*
Osatuke. Comprehensive Psychiatry, 2008, 49, 70-77 (Year: 2008).*
Lee. The Journal of Pharmacology and Experimental Therapeutics, 2007, 321, 823-829 (Year: 2007).*
GB1519352.7 Search Report, dated Aug. 18, 2016.
International Search Report and Written Opinion; PCT/GB2016/053396, dated Dec. 21, 2016.
Meanwell, Synopsis of some recent tactical application of bioisosteres in drug design. J Med Chem. Apr. 28, 2011;54(8):2529-91.

* cited by examiner

*Primary Examiner* — Noble E Jarrell
(74) *Attorney, Agent, or Firm* — McCarter & English, LLP; Steven G. Davis; Mei Bai

(57) ABSTRACT

This invention relates to compounds that are agonists of the muscarinic $M_1$ and/or $M_4$ receptor and which are useful in the treatment of diseases mediated by the muscarinic $M_1$ and $M_4$ receptors. Also provided are pharmaceutical compositions containing the compounds and the therapeutic uses of the compounds. Compounds provided are of formula (I) where p; q; $X^1$; $X^2$; Y; $R^1$; $R^2$; $R^3$; $R^4$; $R^5$ and $R^6$ are as defined herein.

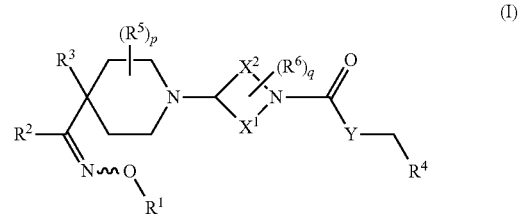

16 Claims, No Drawings

OXIME COMPOUNDS AS AGONISTS OF THE MUSCARINIC M1 AND/OR M4 RECEPTOR

RELATED APPLICATIONS

This application is a 35 U.S.C. § 371 national stage filing of International Application No. PCT/GB2016/053396, filed on Nov. 2, 2016, which claims priority to United Kingdom Patent Application No. 1519352.7, filed on Nov. 2, 2015.

This invention relates to a class of novel oxime compounds, their salts, pharmaceutical compositions containing them and their use in therapy of the human body. In particular, the invention is directed to a class of compounds, which are agonists of the muscarinic $M_1$ and/or $M_4$ receptors, and hence are useful in the treatment of Alzheimer's disease, schizophrenia, cognitive disorders and other diseases mediated by the muscarinic $M_1/M_4$ receptors, as well as the treatment or alleviation of pain.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 Br J Pharmacol). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 Br J Pharmacol).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 Science). In schizophrenia, which is also characterised by cognitive impairments, mAChR density is reduced in the pre-frontal cortex, hippocampus and caudate putamen of schizophrenic subjects (Dean et al., 2002 Mol Psychiatry). Furthermore, in animal models, blockade or lesion of central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting side effects resulting from stimulation of peripheral $M_2$ and $M_3$ mAChRs including disturbed gastrointestinal motility, bradycardia, nausea and vomiting (www.drugs.com/pro/donepezil.html;
www.drugs.com/pro/rivastigmine.html).

Further discovery efforts have targeted the identification of direct $M_1$ mAChR agonists to target increases in cognitive function. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain sequelae: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, non-amyloidgenic and amyloidgenic. Cleavage of APP by γ-secretase is common to both pathways, but in the former APP is cleaved by an α-secretase to yield soluble APPα. The cleavage site is within the Aβ sequence, thereby precluding its formation. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3xTgAD transgenic mouse, a model of the different components of Alzheimer's disease (Caccamo et al., 2006 Neuron). Finally, the mAChR agonist cevimeline has been shown to give a small, but significant, reduction in cerebrospinal fluid levels of Aβ in Alzheimer's patients, thus demonstrating potential disease modifying efficacy (Nitsch et al., 2000 Neurol).

Furthermore, preclinical studies have suggested that mAChR agonists display an atypical antipsychotic-like profile in a range of pre-clinical paradigms. The mAChR agonist, xanomeline, reverses a number of dopamine driven behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 CNS Drug Rev). Muscarinic receptors have also been implicated in the neurobiology of addiction. The reinforcing effects of cocaine and other addictive substances are mediated by the mesolimbic dopamine system where behavioral and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore xanomeline has been demonstrated to block the effects of cocaine in these models.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 *Arch Neurol*). This compound was also assessed in a small Phase II study of schizophrenics and gave a significant reduction in positive and negative symptoms when compared to placebo control (Shekhar et al., 2008 *Am J Psych*). However, in all clinical studies xanomeline and other related mAChR agonists have displayed an unacceptable safety margin with respect to cholinergic side effects, including nausea, gastrointestinal pain, diarrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 *Bioorg Med Chem Lett*; Johnson et al., 2010 *Bioorg Med Chem Lett*; Budzik et al., 2010 *ACS Med Chem Lett*). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

THE INVENTION

The present invention provides compounds having activity as muscarinic $M_1$ and/or $M_4$ receptor agonists. More particularly, the invention provides compounds that exhibit selectivity for the $M_1$ or $M_4$ receptor relative to the $M_2$ and $M_3$ receptor subtypes.

Accordingly, in a first embodiment (Embodiment 1.1), the invention provides a compound of the formula (1):

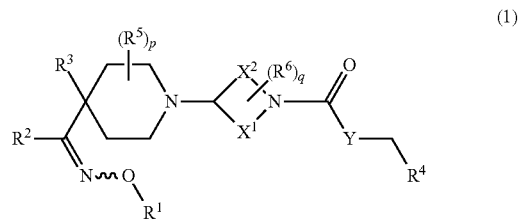

or a salt thereof, wherein:

p is 0, 1 or 2;
q is 0, 1 or 2;
Y is N, O, S or C;
$X^1$ and $X^2$ are saturated hydrocarbon groups which together contain a total of four to nine carbon atoms and which link together such that the moiety:

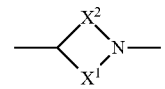

forms a mono or bicyclic ring system;

$R^1$ is a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^2$ is cyano or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^3$ is selected from hydrogen; halogen; cyano; hydroxy; $C_{1-3}$ alkoxy; and a $C_{1-5}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^4$ is a H or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$ is fluorine; and
$R^6$ is fluorine.

1.2 A compound according to Embodiment 1.1 wherein $R^1$ is a $C_{1-6}$ non-aromatic hydrocarbon group containing 0, 1 or 2 carbon-carbon multiple bonds, wherein the hydrocarbon group is optionally substituted with one to six fluorine atoms and wherein one or two, but not all, carbon atoms of the hydrocarbon group may optionally be replaced by a heteroatom selected from O, N and S and oxidised forms thereof.

1.3 A compound according to either of Embodiments 1.1 and 1.2 wherein $R^1$ is selected from $C_{1-6}$ alkyl; $C_{2-5}$ alkenyl; $C_{2-6}$ alkynyl; and $C_{1-6}$ non-aromatic hydrocarbon groups consisting of or containing a $C_{3-6}$ cycloalkyl or $C_{5-6}$ cycloalkenyl group; each of the said alkyl, alkenyl, alkynyl and non-aromatic hydrocarbon groups being optionally substituted with one to six fluorine atoms and wherein one or two, but not all, carbon atoms of each of the alkyl, alkenyl, alkynyl and non-aromatic hydrocarbon groups may optionally be replaced by a heteroatom selected from O, N and S and oxidised forms thereof.

1.4 A compound according to any one of Embodiments 1.1 to 1.3 wherein $R^1$ is $C_{1-4}$ alkyl.

1.5 A compound according to Embodiment 1.4 wherein $R^1$ is selected from:
methyl
ethyl;
propyl;
isopropyl;
butyl.

1.6 A compound according to any one of Embodiments 1.1 to 1.5 wherein $R^2$ is selected from cyano; $C_{1-6}$ alkyl; $C_{2-5}$ alkenyl; $C_{2-6}$ alkynyl; and $C_{1-6}$ non-aromatic hydrocarbon groups consisting of or containing a $C_{3-6}$ cycloalkyl or $C_{5-6}$ cycloalkenyl group; each of the said alkyl, alkenyl, alkynyl and non-aromatic hydrocarbon groups being optionally substituted with one to six fluorine atoms and wherein one or two, but not all, carbon atoms of each of the alkyl, alkenyl, alkynyl and non-aromatic hydrocarbon groups may optionally be replaced by a heteroatom selected from O, N and S and oxidised forms thereof.

1.7 A compound according to any one of Embodiments 1.1 to 1.6 wherein $R^2$ is $C_{1-4}$ alkyl.

1.8 A compound according to Embodiment 1.7 wherein $R^2$ is selected from:
methyl
ethyl;
propyl;
isopropyl;
butyl.

1.9 A compound according to Embodiments 1.1 to 1.8 wherein $R^1$ and $R^2$ are independently methyl, ethyl, propyl or isopropyl.

1.10 A compound according to Embodiment 1.1 wherein $R^3$ is H or a $C_{1-6}$ non-aromatic hydrocarbon group containing 0, 1 or 2 carbon-carbon multiple bonds, wherein the hydrocarbon group is optionally substituted with one to six fluorine atoms and wherein one or two, but not all, carbon atoms of the hydrocarbon group may optionally be replaced by a heteroatom selected from O, N and S and oxidised forms thereof.

1.11 A compound according to either of Embodiment 1.10 wherein $R^3$ is selected from H; $C_{1-6}$ alkyl; $C_{2-5}$ alkenyl; $C_{2-6}$ alkynyl; and $C_{1-6}$ non-aromatic hydrocarbon groups consisting of or containing a $C_{3-6}$ cycloalkyl or $C_{5-6}$ cycloalkenyl group; each of the said alkyl, alkenyl, alkynyl and non-aromatic hydrocarbon groups being optionally substituted with one to six fluorine atoms and wherein one or two, but not all, carbon atoms of each of the alkyl, alkenyl, alkynyl and non-aromatic hydrocarbon groups may optionally be replaced by a heteroatom selected from O, N and S and oxidised forms thereof.

1.12 A compound according to any one of Embodiments 1.1 to 1.11 wherein $R^3$ is selected from hydrogen, halogen, cyano, hydroxy, $C_{1-3}$ alkoxy and $C_{1-4}$ alkyl.

1.13 A compound according to Embodiment 1.12 wherein $R^3$ is selected from hydrogen, fluorine, methyl and methoxy.

1.14 A compound according to Embodiment 1.13 wherein $R^3$ is selected from hydrogen, fluorine and methoxy.

1.15 A compound according to Embodiment 1.14 wherein $R^3$ is selected from hydrogen and fluorine.

1.16 A compound according to Embodiment 1.15 wherein $R^3$ is hydrogen.

1.17 A compound according to Embodiment 1.16 wherein $R^3$ is fluorine.

1.18 A compound according to any one of Embodiments 1.1 to 1.17 wherein $R^4$ is H or an acyclic $C_{1-4}$ hydrocarbon group optionally substituted with one or more fluorine atoms.

1.19 A compound according to Embodiment 1.18 wherein $R^4$ is H or an acyclic $C_{1-3}$ hydrocarbon group optionally substituted with one or more fluorine atoms.

1.20 A compound according to Embodiment 1.19 wherein $R^4$ is H or a $C_{1-3}$ alkyl group or a $C_{1-2}$ alkynyl group.

1.21 A compound according to Embodiment 1.20 wherein $R^4$ is selected from H, methyl, fluoromethyl, ethyl, ethynyl and 1-propynyl.

1.22 A compound according to Embodiment 1.21 wherein $R^4$ is methyl.

1.23 A compound according to Embodiment 1.21 wherein $R^4$ is H.

1.24 A compound according to any one of Embodiments 1.1 to 1.23 wherein p is 0 or 1.

1.25 A compound according to Embodiment 1.35 wherein p is 0.

1.26 A compound according to Embodiment 1.35 wherein p is 1.

1.27 A compound according to any one of Embodiments 1.1 to 1.26 wherein q is 0 or 1.

1.28 A compound according to Embodiment 1.27 wherein q is 0.

1.29 A compound according to Embodiment 1.27 wherein q is 1.

1.30 A compound according to any one of Embodiments 1.1 to 1.29 wherein Y is N, O or $CH_2$.

1.31 A compound according to Embodiment 1.30 wherein Y is N.

1.32 A compound according to Embodiment 1.30 wherein Y is O.

1.33 A compound according to Embodiment 1.30 wherein Y is S.

1.34 A compound according to any one of Embodiments 1.1 to 1.33 wherein the bicyclic ring system formed by the moiety:

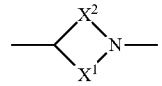

is selected from:
(a) piperidine;
(b) azepane;
(a) an azabicyclo-octane or azabicyclo-nonane ring system;
(b) a 2-aza-spiro[3.4]octane or a 6-aza-spiro[3.4]octane ring system; and (c) a cyclopentanopyrrolidine ring system.

1.34 A compound according to any one of Embodiments 1.1 to 1.33 wherein $X^1$ and $X^2$ together contain four to seven carbon atoms.

1.35 A compound according to any one of Embodiments 1.1 to 1.34 wherein the bicyclic ring system formed by the moiety:

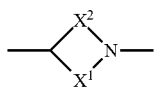

is a bridged bicyclic ring system.

1.36 A compound according to Embodiment 1.35 wherein the bridged bicyclic ring system is an azabicyclo-octane or azabicyclo-nonane ring system.

1.37 A compound according to Embodiment 1.36 wherein the bridged bicyclic ring system is selected from an 8-aza-bicyclo[3.2.1]octane ring system, a 9-aza-bicyclo[3.3.1]nonane ring system and a 6-aza-bicyclo[3.2.1]octane ring system.

1.38 A compound according to any one of Embodiments 1.1 to 1.34 wherein the bicyclic ring system formed by the moiety:

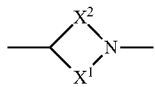

is a spirocyclic ring system.

1.39 A compound according to Embodiment 1.38 wherein the spirocyclic ring system is a 2-aza-spiro[3.4]octane or a 6-aza-spiro[3.4]octane ring system.

1.40 A compound according to any one of Embodiments 1.1 to 1.34 wherein the bicyclic ring system formed by the moiety:

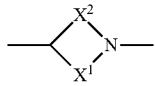

is a fused bicyclic ring system.

1.41 A compound according to Embodiment 1.40 wherein the fused bicyclic ring system is a cyclopentanopyrrolidine ring system.

1.42 A compound according to any one of Embodiments 1.1 to 1.41 wherein the bicyclic ring system formed by the moiety:

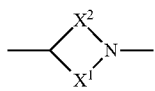

is selected from ring systems below:

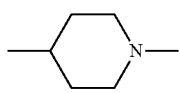
A

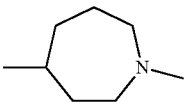
B

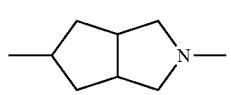
C

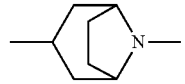
D

E

F

G

H

I

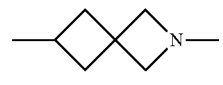
J 1.43 A compound according to Embodiment 1.1 having the formula (2):

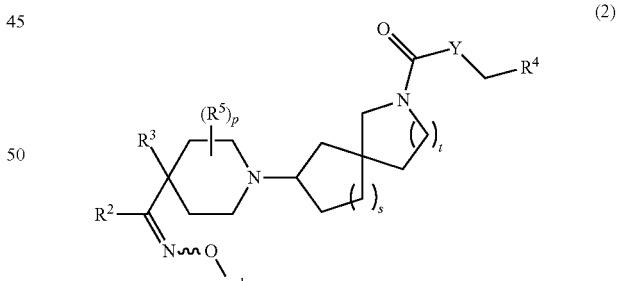
(2)

wherein $R^1$, $R^2$, $R^3$, $R^4$, $R^5$, Y and p are as defined in any one of Embodiments 1.1 to 1.34; s is 0 or 1 and t is 0 or 1.

1.44 A compound according to Embodiment 1.43 wherein the total of s and t is 1.

1.45 A compound according to Embodiment 1.44 wherein s is 0 and t is 1.

1.46 A compound according to Embodiment 1.44 wherein s is 1 and t is 0.

1.47 A compound according to Embodiment 1.1 having the formula (3):

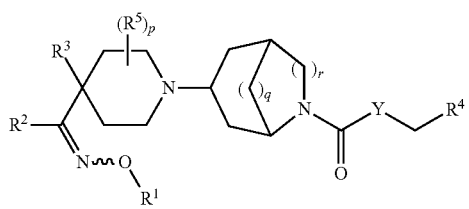

(3)

wherein $R^1$, $R^2$, $R^3$, $R^4$, $R^5$, Y and p are as defined in any one of Embodiments 1.1 to 1.34; q is 1, 2 or 3 and r is 0 or 1, provided that the total of q and r is 2 or 3.

1.48 A compound according to Embodiment 1.47 wherein (i) r is 0 and q is 2; (ii) r is 0 and q is 3; or (iii) r is 1 and q is 1.

1.49 A compound according to Embodiment 1.1 having the formula (4):

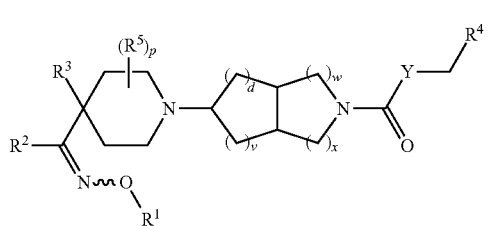

(4)

wherein $R^1$, $R^2$, $R^3$, $R^4$, $R^5$, Y and p are as defined in any one of Embodiments 1.1 to 1.34; and u, v, w and x are each 0, 1 or 2 provided that the total u+v+w+x is at least 1 and does not exceed 5.

1.50 A compound according to Embodiment 1.49 wherein each of u, v, w and x is 1.

1.51 A compound according to Embodiment 1.1 which is as defined in any one of Examples 1-1 to 4-1.

1.52 A compound according to any one of Embodiments 1.1 to 1.50 having a molecular weight of less than 550, for example less than 500, or less than 450.

1.53 A compound according to any one of Embodiments 1.1 to 1.52 which is in the form of a salt.

1.54 A compound according to Embodiment 1.53 wherein the salt is an acid addition salt.

1.55 A compound according to Embodiment 1.53 or Embodiment 1.54 wherein the salt is a pharmaceutically acceptable salt.

Definitions

In this application, the following definitions apply, unless indicated otherwise.

The term "treatment", in relation to the uses of the compounds of the formulas (1) to (4), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" (as in "$C_{1-5}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" and "cycloalkenyl" are used in their conventional sense (e.g. as defined in the IUPAC Gold Book) unless indicated otherwise.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^2$, $R^3$ and $R^4$ above, where stated, one or two but not all, carbon atoms of the non-aromatic hydrocarbon group may optionally be replaced by a heteroatom selected from O, N and S and oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—$S(O)_2$—$CH_2$—, replacement of a carbon atom in a —$CH_2$—$CH_2$—$CH_2$-chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formulas (1) to (4) can exist in the form of salts, for example acid addition salts or, in certain cases salts of organic and inorganic bases such as carboxylate, sulfonate and phosphate salts. All such salts are within the scope of this invention, and references to compounds of the formulas (1) to (4) include the salt forms of the compounds as defined in Embodiments 1.53 to 1.55.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.54) may be formed with a wide variety of acids, both inorganic and organic. Examples of acid addition salts falling within Embodiment 1.54 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) contain an amine function, these may form quaternary ammonium salts (Embodiment 1.72), for example by reaction with an alkylating agent according to methods well known to the skilled person. Such quaternary ammonium compounds are within the scope of formula (1).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.73), the invention provides a geometric isomer of a compound according to any one of Embodiments 1.1 to 1.72.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.74) the invention provides a compound according to any one of Embodiments 1.1 to 1.73 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.75), the invention provides compositions containing a compound according to Embodiment 1.74 having one or more chiral centres, wherein at least 55% (e.g. at least 60%, 65%, 70%, 75%, 80%, 85%, 90% or 95%) of the compound of Embodiment 1.73 is present as a single optical isomer (e.g. enantiomer or diastereoisomer).

In one general embodiment (Embodiment 1.76), 99% or more (e.g. substantially all) of the total amount of the compound (or compound for use) of Embodiment 1.74 is present as a single optical isomer.

For example, in one embodiment (Embodiment 1.77) the compound is present as a single enantiomer.

In another embodiment (Embodiment 1.78), the compound is present as a single diastereoisomer.

The invention also provides mixtures of optical isomers, which may be racemic or non-racemic. Thus, the invention provides:

1.79 A compound according to Embodiment 1.74 which is in the form of a racemic mixture of optical isomers.

1.80 A compound according to Embodiment 1.74 which is in the form of a non-racemic mixture of optical isomers.

Isotopes

The compounds of the invention as defined in any one of Embodiments 1.1 to 1.80 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.81), the compound of any one of Embodiments 1.1 to 1.80 contains no radioactive isotopes. Such compounds are preferred for therapeutic use. In another embodiment (Embodiment 1.82), however, the compound of any one of Embodiments 1.1 to 1.80 may contain one or more radioisotopes. Compounds containing such radioisotopes may be useful in a diagnostic context.

Solvates

Compounds of the formula (1) as defined in any one of Embodiments 1.1 to 1.82 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.83 and 1.84, the invention provides:

1.83 A compound according to any one of Embodiments 1.1 to 1.82 in the form of a solvate.

1.84 A compound according to Embodiment 1.83 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.85), the invention provides a compound as defined in any one of Embodiments 1.1 to 1.83 in an anhydrous form (e.g. anhydrous crystalline form).

Crystalline and Amorphous Forms

The compounds of any one of Embodiments 1.1 to 1.83 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.86 A compound according to any one of Embodiments 1.1 to 1.85 in a crystalline form.

1.80 A compound according to any one of Embodiments 1.1 to 1.85 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.88 A compound according to any one of Embodiments 1.1 to 1.85 which is in an amorphous form.

Prodrugs

The compounds of the formula (1) as defined in any one of Embodiments 1.1 to 1.88 may be presented in the form of a pro-drug. By "prodrugs" is meant for example any compound that is converted in vivo into a biologically active compound of the formula (1), as defined in any one of Embodiments 1.1 to 1.88.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.89), the invention provides a pro-drug of a compound as defined in any one of Embodiments 1.1 to 1.82 wherein the compound contains a functional group which is convertible under physiological conditions to form a hydroxyl group or amino group.

Complexes and Clathrates

Also encompassed by formula (1) in Embodiments 1.1 to 1.89 are complexes (e.g. inclusion complexes or clathrates with compounds such as cyclodextrins, or complexes with metals) of the compounds of Embodiments 1.1 to 1.89.

Accordingly, in another embodiment (Embodiment 1.90), the invention provides a compound according to any one of Embodiments 1.1 to 1.89 in the form of a complex or clathrate.

Biological Activity and Therapeutic Uses

The compounds of the present invention have activity as muscarinic $M_1$ and/or $M_4$ receptor agonists. The muscarinic activity of the compounds can be determined using the Phospho-ERK1/2 assay described in Example A below.

A significant advantage of compounds of the invention is that they are highly selective for the $M_1$ and/or $M_4$ receptors relative to the $M_2$ and $M_3$ receptor subtypes.

Compounds of the invention are neither agonists nor antagonists of the $M_2$ and $M_3$ receptor subtypes. For example, whereas compounds of the invention typically have $pEC_{50}$ values of at least 6 (preferably at least 6.5) and $E_{max}$ values of greater than 80 (preferably greater than 95) against the $M_1$ and/or $M_4$ receptor in the functional assay described in Example A, they may have $pEC_{50}$ values of less than 5 and $E_{max}$ values of less than 20% when tested against the $M_2$ and $M_3$ subtypes in the functional assay of Example A.

Some compounds of the invention have activity at both the $M_1$ and $M_4$ receptors, and some have activity at the $M_4$ receptor.

Accordingly, in Embodiments 2.1 to 2.15, the invention provides:

2.1 A compound according to any one of Embodiments 1.1 to 1.90 for use in medicine.

2.2 A compound according to any one of Embodiments 1.1 to 1.90 for use as a muscarinic $M_1$ and/or $M_4$ receptor agonist.

2.3 A compound according to any one of Embodiments 1.1 to 1.90 which is a muscarinic $M_1$ receptor agonist having a $pEC_{50}$ greater than 6.9 and an $E_{max}$ of at least 80 against the $M_1$ receptor in the assay of Example A herein or an assay substantially similar thereto.

2.4 A compound according to Embodiment 2.3 which is a muscarinic $M_1$ receptor agonist having a $pEC_{50}$ greater than 7.0.

2.5 A compound according to Embodiment 2.3 or Embodiment 2.4 having an $E_{max}$ of at least 90 against the $M_1$ receptor.

2.6 A compound according to any one of Embodiments 1.1 to 1.90 which is a muscarinic $M_1$ and $M_4$ receptor agonist having a $pEC_{50}$ in the range from 6.0 to 7.8 and an $E_{max}$ of at least 70 against the muscarinic $M_1$ and $M_4$ receptors in the assay of Example A herein or an assay substantially similar thereto.

2.7 A compound according to any one of Embodiments 1.1 to 1.90 which is a muscarinic $M_4$ receptor agonist having a $pEC_{50}$ greater than 7.0.

2.8 A compound according to Embodiment 2.6 or Embodiment 2.7 having an $E_{max}$ of at least 90 against the $M_4$ receptor.

2.9 A compound according to any one of Embodiments 1.1 to 1.90 which is a muscarinic $M_4$ receptor agonist having a $pEC_{50}$ in the range from 6.0 to 7.8 and an $E_{max}$ of at least 70 against the muscarinic $M_4$ receptor in the assay of Example A herein or an assay substantially similar thereto.

2.10 A compound according to any one of Embodiments 2.3 to 2.9 which is selective for the $M_1$ and $M_4$ receptor compared to the muscarinic $M_2$ and $M_3$ receptors.

2.11 A compound according to Embodiment 2.9 which is selective for the $M_4$ receptor compared to the muscarinic $M_2$ and $M_3$ receptors.

2.12 A compound according to any one of Embodiments 2.3 to 2.5 which is selective for the $M_1$ receptor compared to the muscarinic $M_2$, $M_3$ and $M_4$ receptors.

2.13 A compound according to any one of Embodiments 2.7 or 2.9 which is selective for the $M_4$ receptor compared to the muscarinic $M_1$, $M_2$ and $M_3$ receptors.

2.14 A compound according to any one of Embodiments 2.3 to 2.13 which has a $pEC_{50}$ of less than 5 and an $E_{max}$ of less than 50 against the muscarinic $M_2$ and $M_3$ receptor subtypes.

2.15 A compound according to Embodiment 2.14 which has a $pEC_{50}$ of less than 4.5 and/or an $E_{max}$ of less than 30 against the muscarinic $M_2$ and $M_3$ receptor subtypes.

2.16 A compound according to any one of Embodiments 1.1 to 1.90 and Embodiments 2.3 to 2.15 for use in the treatment of a disease or condition mediated by the muscarinic $M_1$ and/or $M_4$ receptors.

By virtue of their muscarinic $M_1$ and/or $M_4$ receptor agonist activity, compounds of the invention can be used in the treatment of Alzheimer's disease, schizophrenia and other psychotic disorders, cognitive disorders and other diseases mediated by the muscarinic $M_1$ and/or $M_4$ receptor, and can also be used in the treatment of various types of pain.

Accordingly, in Embodiments 2.17 to 2.38, the invention provides:

2.17 A compound according to any one of Embodiments 1.1 to 1.90 for use in the treatment of a cognitive disorder or psychotic disorder.

2.18 A compound for use in according to Embodiment 2.17 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as multi-infarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, *cannabis*, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders and schizo-affective disorder.

2.19 A compound according to any one of Embodiments 1.1 to 1.90 for use in the treatment of Alzheimer's disease.

2.20 A compound according to any one of Embodiments 1.1 to 1.90 for use in the treatment of Schizophrenia.

2.21 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.90.

2.22 A method according to Embodiment 2.21 wherein the cognitive disorder comprises, arises from or is associated with a condition as defined in Embodiment 2.18.

2.23 A method according to Embodiment 2.22 wherein the cognitive disorder arises from or is associated with Alzheimer's disease.

2.24 A method according to Embodiment 2.22 wherein the cognitive disorder is Schizophrenia.

2.25 The use of a compound according to any one of Embodiments 1.1 to 1.90 for the manufacture of a medicament for the treatment of a cognitive disorder.

2.26 The use according to Embodiment 2.25 wherein the cognitive disorder comprises, arises from or is associated with a condition as defined in Embodiment 2.18.

2.27 The use according to Embodiment 2.26 wherein the cognitive disorder arises from or is associated with Alzheimer's disease.

2.28 The use according to Embodiment 2.26 wherein the cognitive disorder is Schizophrenia.

2.29 A compound according to any one of Embodiments 1.1 to 1.90 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.30 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.90.

2.31 A compound according to any one of Embodiments 1.1 to 1.90 for the treatment of peripheral disorders such as reduction of intra ocular pressure in Glaucoma and treatment of dry eyes and dry mouth including Sjogren's Syndrome.

2.32 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.90.

2.33 The use of a compound according to any one of Embodiments 1.1 to 1.90 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.34 The use of a compound according to any one of Embodiments 1.1 to 1.90 for the use in the treatment of skin lesions for example due to pemphigus vulgaris, dermatitis herpetiformis, pemphigoid and other blistering skin conditions.

2.35 The use of a compound according to any one of Embodiments 1.1 to 1.90 for the use in treating, preventing, ameliorating or reversing conditions associated with altered gastro-intestinal function and motility such as functional dyspepsia, irritable bowel syndrome, gastroesophageal acid reflux (GER) and esophageal dysmotility, symptoms of gastroparesis and chronic diarrhea.

2.36 The use of a compound according to any one of Embodiments 1.1 to 1.90 for the use in the treatment of olfactory dysfunction such as Bosma-Henkin-Christiansen syndrome, chemical poisoning (e.g. selenium and silver), hypopituitarism, Kallmann Syndrome, skull fractures, tumour therapy and underactive thyroid gland.

2.37 The use of a compound according to any one of Embodiments 1.1 to 1.90 for the treatment of addiction.

2.38 The use of a compound according to any one of Embodiments 1.1 to 1.90 for the treatment of movement disorders such as Parkinson's disease, ADHD, Huntingdon's disease, tourette's syndrome and other syndromes associated with dopaminergic dysfunction as an underlying pathogenetic factor driving disease.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.90, which process comprises:

(A) the reaction of a compound of the formula (10)

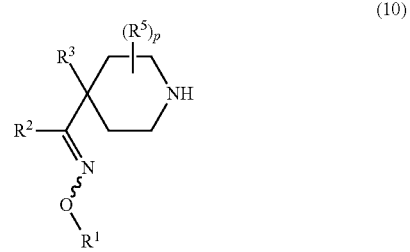

(10)

with a compound of the formula (11):

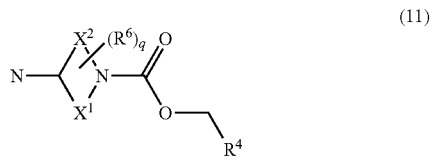

(11)

under reductive amination conditions; wherein $R^1$, $R^2$, $R^3$, $R^4$, $R^5$, $R^6$, $X^1$, $X^2$, p and q are as defined in any one of Embodiments 1.1 to 1.90; or
(B) the reaction of a compound of the formula (12):

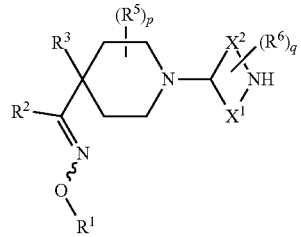
(12)

with a compound of the formula Cl—C(=O)—CH$_2$—R$^4$, in the presence of a base; or
(C) the reaction of a compound of the formula (10)

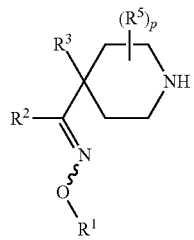
(10)

with a compound of the formula (13):

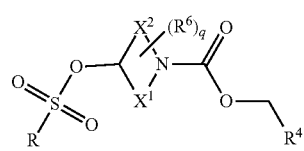
(13)

under nucleophilic substitution conditions; wherein $R^1$, $R^2$, $R^3$, $R^4$, $R^5$, $R^6$, $X^1$, $X^2$, p and q are as defined in any one of Embodiments 1.1 to 1.90; and optionally:
(D) the reaction of a compound of the formula (14):

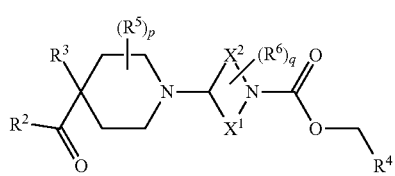
(14)

with a compound of the formula NH$_2$OR$^1$; or
(E) the reaction of a compound of the formula (15):

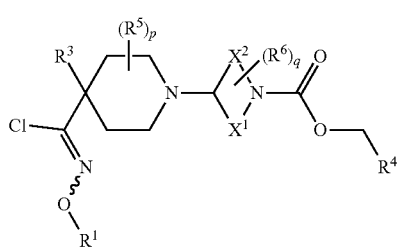
(15)

with a compound of the formula NH$_2$R$^2$, in the presence of a base; or
(F) the reaction of a compound of the formula (15):

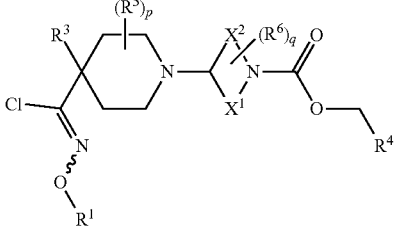
(15)

with a NaCN; or
(G) converting one compound of the formula (1) to another compound of the formula (1).

In process variant (A), the piperidine heterocycle (10) is reacted with the substituted ketone (11) under reductive amination conditions. The reductive amination reaction is typically carried out at ambient temperature to mild heating (e.g. to a temperature of about 20° C. to about 70° C.) using either a borohydride reducing agent such as sodium triacetoxy-borohydride in a solvent such as dichloromethane, dichloroethane or dimethylformamide containing acetic acid, or sodium cyanoborohydride in combination with zinc chloride, or sodium triacetoxy-borohydride in combination with titanium isopropoxide.

Process variant (B) is typically carried out in an aprotic solvent such as dichloromethane or dichloroethane in the presence of a non-interfering base such as triethylamine. The reaction may be conducted at room temperature.

In process variant (C), the piperidine heterocycle (10) is reacted with the sulfonic ester (13, R=methyl, trifluoromethyl or 4-methylphenyl) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide.

Process variant (D) is typically carried out in an protic solvent such as methanol in the presence of a non-interfering base such as sodium acetate. The reaction may be conducted at room temperature.

Process variant (E) is typically carried out in an aprotic solvent such as dichloromethane, dichloroethane or dimethylformamide in the presence of a non-interfering base such as potassium carbonate. The reaction is typically carried out at ambient temperature to moderate heating (e.g. to a temperature of about 20° C. to about 120° C.).

Process variant (F) is typically carried out in an aprotic solvent such as DMSO or dimethylformamide. The reaction is typically carried out at ambient temperature to moderate heating (e.g. to a temperature of about 20° C. to about 120° C.).

Intermediate compounds of the formula (12) can be prepared by the series of reactions shown in Scheme 1 below.

Scheme 1

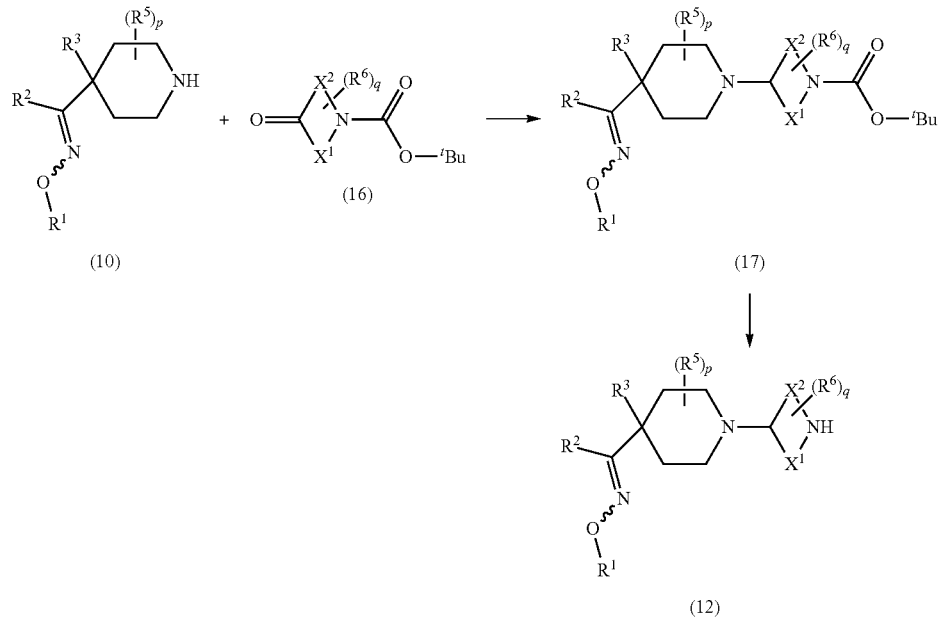

In reaction Scheme 1, the piperidine (10) is reacted with the Boc-protected ketone (12) under reductive amination conditions. The reductive amination reaction is typically carried out with mild heating (e.g. to a temperature of from about 40° C. to about 70° C.) in the presence of either sodium cyanoborohydride in combination with zinc chloride or sodium triacetoxyborohydride in combination with titanium isopropoxide in a solvent such as dichloromethane or dichloroethane containing acetic acid to give an intermediate piperidine compound (17) which is then deprotected by removal of the Boc group by treatment with acid (e.g. trifluoroacetic acid in dichloromethane) to give the compound (12).

Compounds of the formula (14) can be prepared by the sequence of reactions shown in Scheme 2 below.

Scheme 2

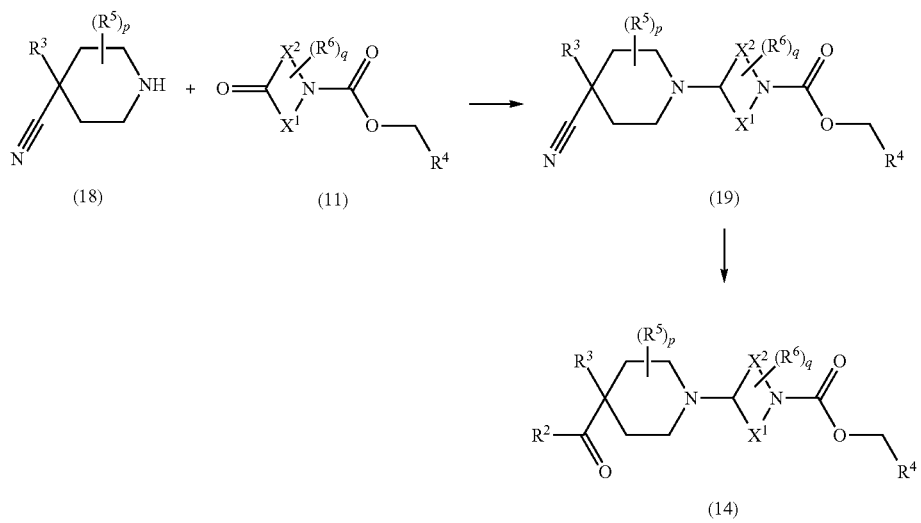

In Scheme 2, the 4-cyanopiperidine derivative (18) is reacted with the ketone (11) under reductive amination conditions of the type described above to give an intermediate 4-cyanopiperidine compound (19) which undergoes selectively addition of a Grignard reagent to give the ketone (14).

Compounds of the formula (15) can also be prepared by the sequence of reactions shown in Scheme 3 below.

with 1-hydroxy-7-azabenzotriazole (HOAt) (L. A. Carpino, J. Amer. Chem. Soc., 1993, 115, 4397) or 1-hydroxybenzotriazole (HOBt) (Konig et al, Chem. Ber., 103, 708, 2024-2034). A preferred amide coupling agent is HATU. The coupling reaction is typically carried out in a non-aqueous, non-protic solvent such as acetonitrile, dioxane, dimethylsulphoxide, dichloromethane, dimethylformamide or N-methylpyrrolidinone, or in an aqueous solvent optionally

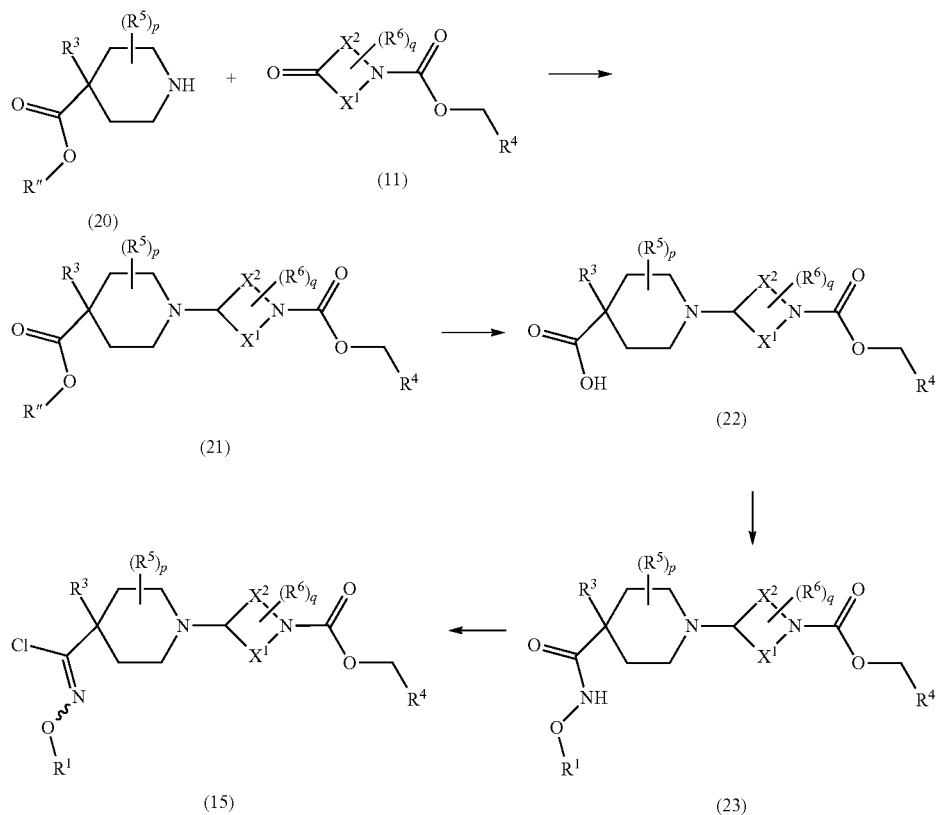

Scheme 3

In reaction Scheme 3, the piperidine ester (20, R″=ethyl or methyl) is reacted with the substituted ketone (13) under reductive amination conditions of the type described above to give an intermediate ester compound (21) which is then selectively hydrolysed under mild conditions using lithium hydroxide or sodium hydroxide to give compound (22). The carboxylic acid (22) is reacted with the compound of formula $NH_2OR^1$ under typical amide coupling conditions to give amide (23). The reaction may be carried out in the presence of a reagent of the type commonly used in the formation of amide bonds. Examples of such reagents include 1,3-dicyclohexylcarbodiimide (DCC) (Sheehan et al, J. Amer. Chem Soc. 1955, 77, 1067), 1-ethyl-3-(3'-dimethylaminopropyl)-carbodiimide (referred to herein either as EDC or EDAC) (Sheehan et al, J. Org. Chem., 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino) phosphonium hexafluorophosphate (PyBOP) (Castro et al, Tetrahedron Letters, 1990, 31, 205). Carbodiimide-based coupling agents are advantageously used in combination together with one or more miscible co-solvents. The reaction can be carried out at room temperature or, where the reactants are less reactive at an appropriately elevated temperature, for example a temperature up to about 100° C., e.g. 50-80° C. The reaction may optionally be carried out in the presence of a non-interfering base, for example a tertiary amine such as triethylamine or N,N-diisopropylethylamine. As an alternative, a reactive derivative of the carboxylic acid, e.g. an anhydride or acid chloride, may be used. The acid chloride is typically reacted with the compound of formula $NH_2OR^1$ in the presence of a base such as sodium bicarbonate. The acid chloride can be prepared using standard methods, for example by treatment of the acid with oxalyl chloride in the presence of a catalytic amount of dimethylformamide.

Treatment of amide (23) with a chlorinating agent, such as thionyl chloride gives the N-alkoxypiperidine-4-carboximidoyl chloride (15).

Once formed, one compound of the formula (1), (2), (3) or (4), or a protected derivative thereof, can be converted into another compound of the formula (1), (2), (3) or (4) by methods well known to the skilled person. Examples of synthetic procedures for converting one functional group into another functional group are set out in standard texts such as *Advanced Organic Chemistry* and Organic Syntheses (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.90 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g. solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 4-1

The compounds of Examples 1-1 to 4-1 shown in Table 1 below have been prepared. Their NMR and LCMS properties and the methods used to prepare them are set out in Table 3. The starting materials for each of the Examples are listed in Table 2.

TABLE 1

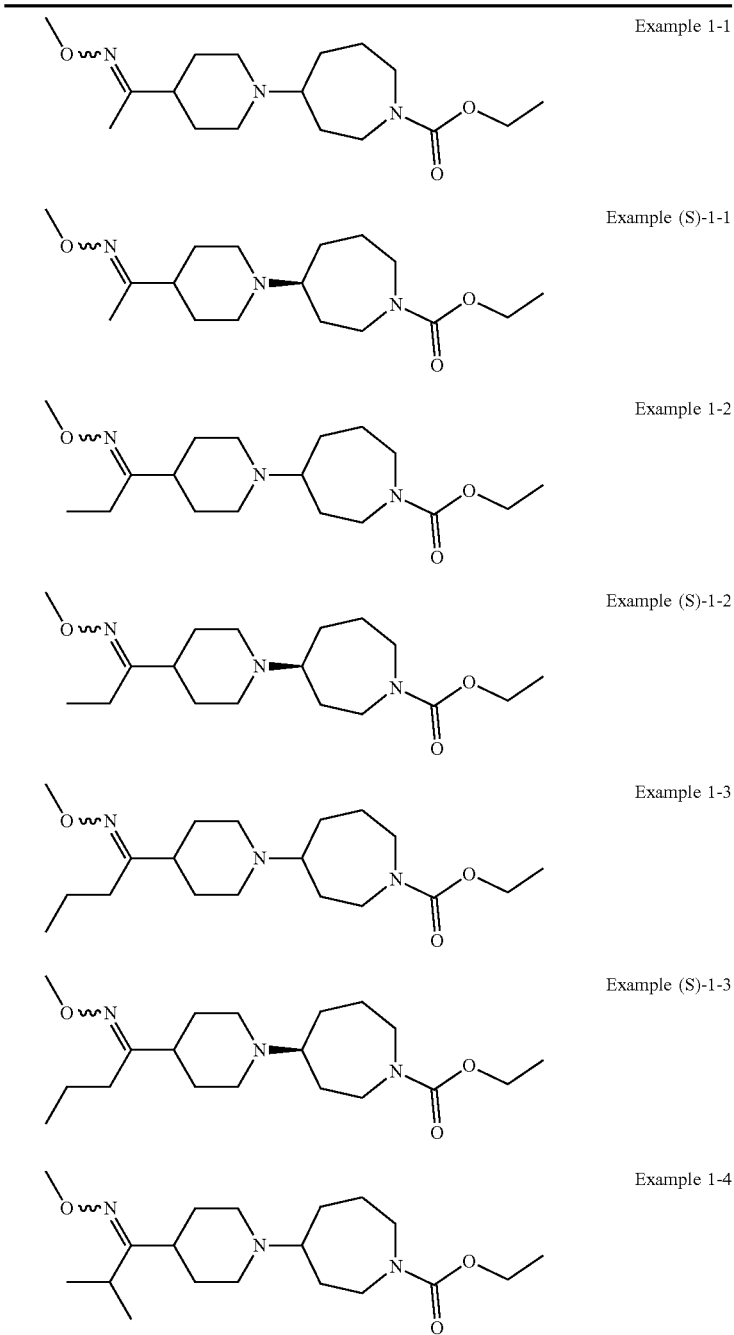

TABLE 1-continued
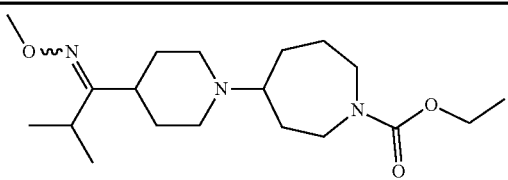
Example 1-5
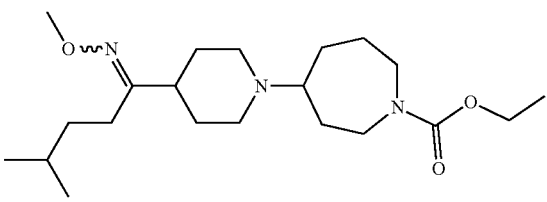 [SMILES: CCOC(=O)N1CCCC(N2CCC(C(CCC(C)C)=NOC)CC2)CC1]
Example 1-6
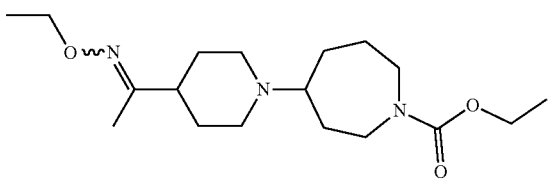 [SMILES: CCON=C(C)C1CCN(C2CCCN(C(=O)OCC)CC2)CC1]
Example 1-7
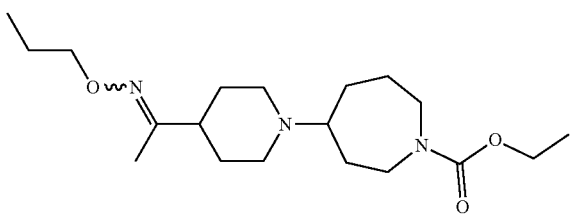 [SMILES: CCCON=C(C)C1CCN(C2CCCN(C(=O)OCC)CC2)CC1]
Example 1-8
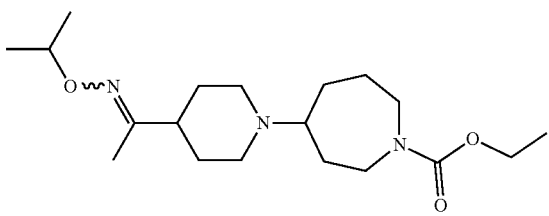 [SMILES: CCOC(=O)N1CCCC(N2CCC(C(C)=NOC(C)C)CC2)CC1]
Example 1-9
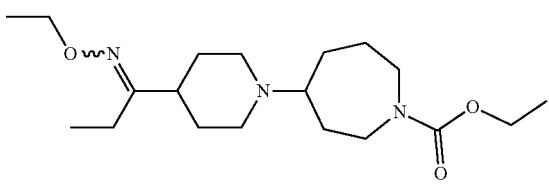 [SMILES: CCON=C(CC)C1CCN(C2CCCN(C(=O)OCC)CC2)CC1]
Example 1-10
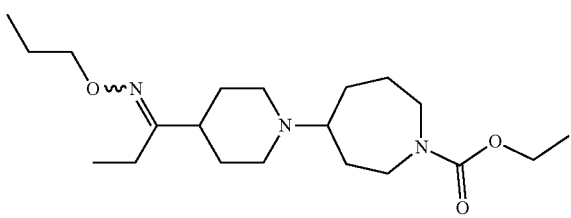 [SMILES: CCCON=C(CC)C1CCN(C2CCCN(C(=O)OCC)CC2)CC1]
Example 1-11
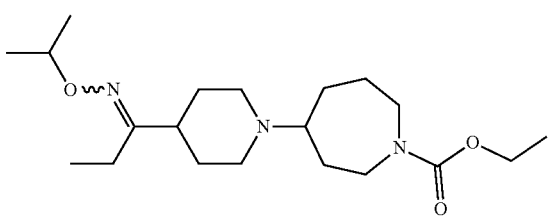 [SMILES: CCOC(=O)N1CCCC(N2CCC(C(CC)=NOC(C)C)CC2)CC1]
Example 1-12

TABLE 1-continued

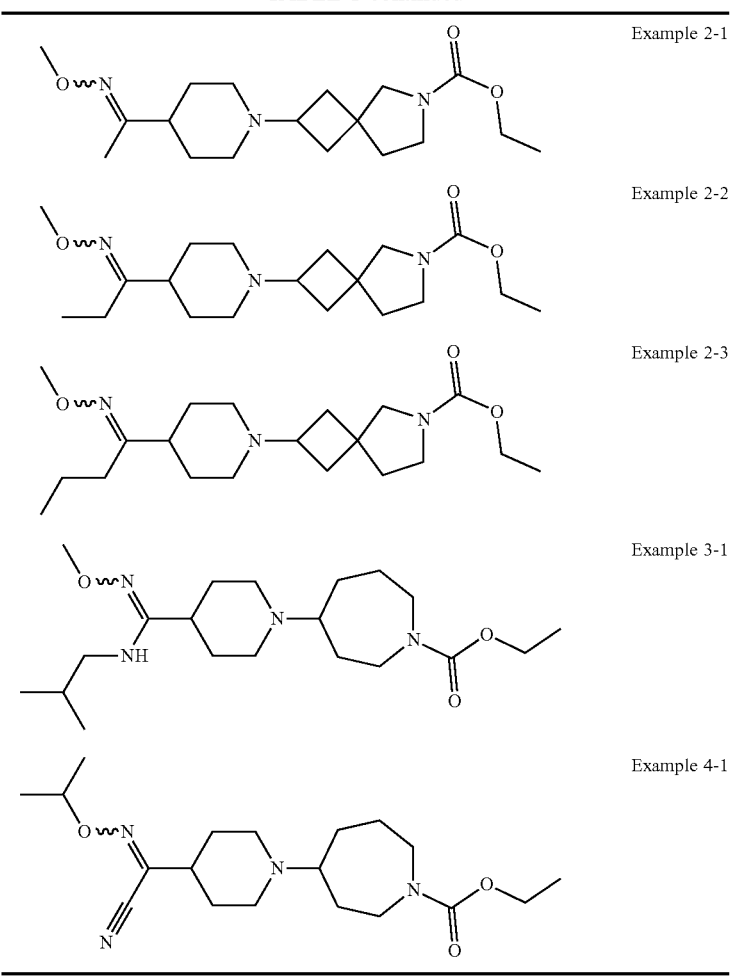

| | |
|---|---|
| | Example 2-1 |
| | Example 2-2 |
| | Example 2-3 |
| | Example 3-1 |
| | Example 4-1 |

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker, Varian or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and Silica gel F254 (Merck) as a stationary phase. Microwave-mediated reactions were performed in Biotage Initiator or CEM Discover microwave reactors.

LCMS experiments were typically carried out using electrospray conditions as specified for each compound under the following conditions:

LCMS Methods A and B

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method A: 0.00/2, 0.10/2, 2.50/95, 3.50/95, 3.55/2, 4.00/2 or Method B: 0.00/2, 0.10/2, 8.40/95, 9.40/95, 9.50/2, 10.00/2; Solvents: solvent C=2.5 L H$_2$O+2.5 mL ammonia solution; solvent D=2.5 L MeCN+135 mL H$_2$O+2.5 mL ammonia solution); Injection volume 3 μL; UV detection 230 to 400 nM; column temperature 45° C.; Flow rate 1.5 mL/min.

LCMS Method C:

Instruments: Waters Acquity H Class, Photo Diode Array, SQ Detector; Column: BEH C18, 1.7 micron, 2.1×50 mm; Gradient [time (min)/solvent B in A (%)]: 0.00/5, 0.40/5, 0.8/35, 1.20/55, 2.50/100, 3.30/100 4.00/5; Solvents: solvent A=5 mM Ammonium acetate and 0.1% formic acid in H$_2$O; solvent B=0.1% formic acid in MeCN; Injection volume 2 μL; UV detection 200 to 400 nM; Mass detection 100 to 1200 AMU (+ve electrospray); column at ambient temperature; Flow rate 0.5 mL/min.

LCMS Method D:

Instruments: Waters 2695, Photo Diode Array, ZQ-2000 Detector; Column: X-Bridge C18, 5 micron, 150×4.6 mm; Gradient [time (min)/solvent B in A (%)]: 0.00/10, 5.00/90, 7.00/100, 11.00/100, 11.01/10 12.00/10; Solvents: solvent A=0.1% ammonia in H$_2$O; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

LCMS Method E:

Instruments: Waters 2695, Photo Diode Array, ZQ-2000 Detector; Column: X-Bridge C18, 5 micron, 150×4.6 mm; Gradient [time (min)/solvent B in A (%)]: 0.00/100, 7.00/50, 9.00/0, 11.00/0, 11.01/100, 12.00/100; Solvents: solvent A=0.1% ammonia in $H_2O$; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

LCMS Method F

Instruments: Waters Acquity H Class, Photo Diode Array, SQ Detector; Column: BEH C18, 1.7 micron, 2.1×50 mm; Gradient [time (min)/solvent B in A (%)]: 0.00/5, 0.40/5, 0.8/35, 1.20/55, 2.70/95, 3.30/5, 4.00/5; Solvents: solvent A=5 mM Ammonium acetate and 0.1% formic acid in $H_2O$; solvent B=0.1% formic acid in MeCN; Injection volume 2 µL; UV detection 200 to 400 nM; Mass detection 100 to 1200 AMU (+ve electrospray); column at ambient temperature; Flow rate 0.5 mL/min.

LCMS Method G

Instruments: HP 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]:0.00/2, 0.10/2, 8.40/95, 9.40/95, 9.50/2, 10.00/2; Solvents: solvent C=2.5 L $H_2O$+2.5 mL 28% ammonia in $H_2O$ solution; solvent D=2.5 L MeCN+135 mL $H_2O$+2.5 mL 28% ammonia in $H_2O$ solution); Injection volume 1 µL; UV detection 230 to 400 nM; Mass detection 130 to 800 AMU (+ve and −ve electrospray); column temperature 45 C; Flow rate 1.5 mL/min.

LCMS data in the experimental section are given in the format: Mass ion, retention time, UV activity.

Abbreviations d=day(s)
DCE=dichloroethane
DCM=dichloromethane
DEA=diethylamine
DIPEA=diisopropylethylamine
DMF=dimethylformamide
DMSO=dimethylsulfoxide
DPPA=diphenylphosphoryl azide
ES=electro spray ionisation
$Et_3N$=triethylamine
EtOAc=ethyl acetate
h=hour(s)
HPLC=high performance liquid chromatography
LC=liquid chromatography
LiHMDS=Lithium bis(trimethylsilyl)amide
MeCN=acetonitrile
MeOH=methanol
min=minute(s)
MS=mass spectrometry
$N_2$=nitrogen
NMR=nuclear magnetic resonance
rt=room temperature
sat.=saturated
sol.=solution
STAB=sodium triacetoxyborohydride
TBAF=tetra butyl ammonium fluoride
THF=tetrahydrofuran
TLC=thin layer chromatography
Prefixes n-, s-, i-, t- and tert-have their usual meanings: normal, secondary, iso, and tertiary.

Synthesis of Intermediates:

Route 1

Typical Procedure for the Preparation of Ketones as Exemplified by the Preparation of Intermediate 1, Ethyl 4-(4-Acetylpiperidin-1-Yl)Azepane-1-Carboxylate

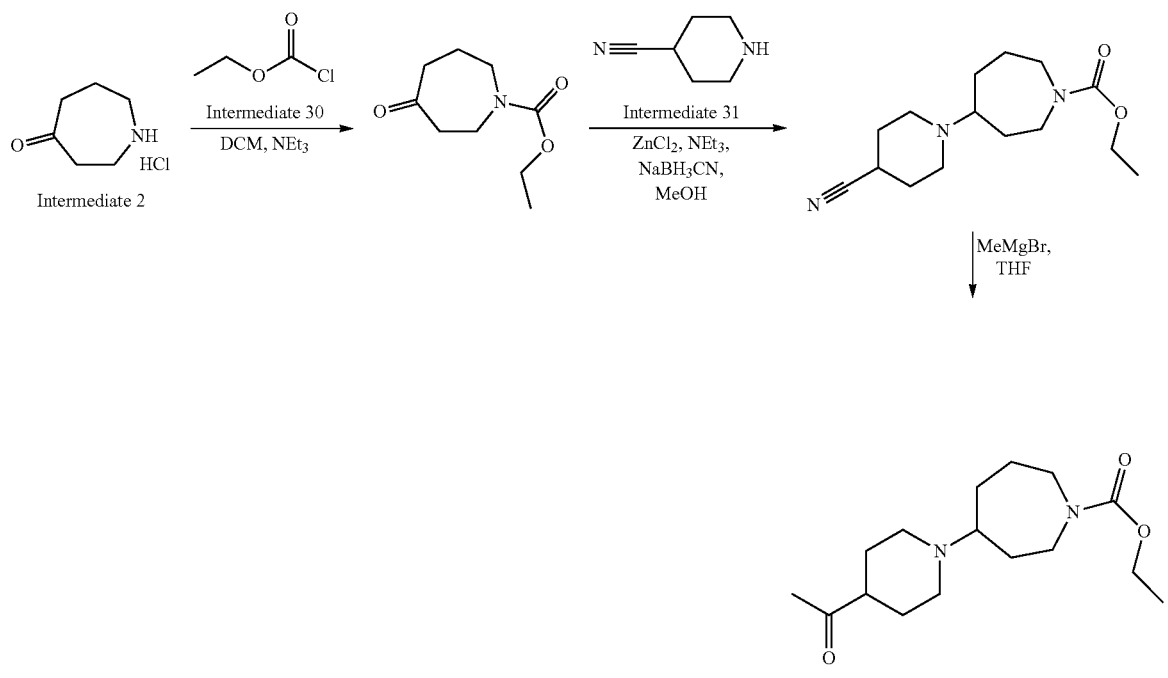

Azepan-4-one.HCl (5.0 g, 44 mmol) and triethylamine (19.0 mL, 133 mmol) were dissolved in DCM (60 mL) and the solution cooled to 0° C. followed by dropwise addition of ethyl chloroformate (6.3 mL, 66 mmol). The resulting reaction mixture was stirred at 25° C. for 3 h and then partitioned between H$_2$O (200 mL) and EtOAc (70 mL). The aqueous layer was further extracted with EtOAc (2×70 mL), combined organics dried over Na$_2$SO$_4$ and solvents removed in vacuo. The crude compound was purified by column chromatography (normal silica, mesh size: 60-120, 0 to 0.5% MeOH in DCM) to give ethyl 4-oxoazepane-1-carboxylate (7.8 g, 95%) as a brown gum.

LCMS (Method C): m/z 186 (M+H)$^+$ (ES$^+$) at 0.87 min, UV active

Ethyl 4-oxoazepane-1-carboxylate (5.0 g, 27 mmol), piperidine-4-carbonitrile (3.0 g, 27 mmol), ZnCl$_2$ (1.1 g, 8 mmol) and triethylamine (19.0 mL, 136 mmol) were dissolved in MeOH (60 mL) and the reaction mixture was stirred at 50° C. for 1 h. The mixture was then cooled to 0° C. before addition of NaBH$_3$CN (6.8 g, 108 mmol) and further stirring at 50° C. for 7 h. The solvents were removed in vacuo and the residue was partitioned between H$_2$O (200 mL) and EtOAc (80 mL). The aqueous layer was extracted with EtOAc (2×80 mL) and combined organics dried (Na$_2$SO$_4$) and concentrated in vacuo. The crude was purified by column chromatography (normal silica, mesh size: 60-120, 0 to 2.0% MeOH in DCM) to give ethyl 4-(4-cyanopiperidin-1-yl)azepane-1-carboxylate (4.0 g, 53%) as a colourless gum.

LCMS (Method D): m/z 280 (M+H)$^+$ (ES$^+$) at 5.13 min, UV active

Ethyl 4-(4-cyanopiperidin-1-yl)azepane-1-carboxylate (300 mg, 0.11 mmol) was dissolved in THF (5 mL) and cooled to 0° C. Methyl magnesium bromide (3 M in ether) (1.5 mL, 4.46 mmol) was added dropwise and the resulting reaction mixture stirred at rt for 4 h. The reaction mixture was diluted with water (50 mL) and extracted with EtOAc (30 mL). The aqueous layer was further extracted with EtOAc (2×30 mL) and combined organics dried (Na$_2$SO$_4$) and concentrated in vacuo. The crude compound was purified by column chromatography (normal silica, mesh size: 60-120, 2.0 to 5.0% MeOH in DCM) to give ethyl 4-(4-acetylpiperidin-1-yl)azepane-1-carboxylate (210 mg, 66%) as a colourless gum.

The data for the title compound are in Table 2

Route 2

Typical Procedure for the Preparation of Grignard Reagents, as Exemplified by the Preparation of Isopentylmagnesium Bromide

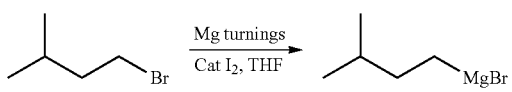

To activated magnesium turnings (1.2 g, 49.7 mmol) and iodine (cat.) was added anhydrous THF (5 mL). To the mixture was added 1-bromo-3-methylbutane (5.0 g, 33.1 mmol) dropwise and the reaction initiated with a heat gun. The resulting reaction mixture was diluted with anhydrous THF (35 mL) and the reaction further stirred for 2 h at 60° C. The crude mixture was used directly for the next step.

Route 3

Typical Procedure for the Preparation of Ketones, as Exemplified by the Preparation of Intermediate 11, Ethyl (4S)-4-(4-Acetylpiperidin-1-Yl)Azepane-1-Carboxylate

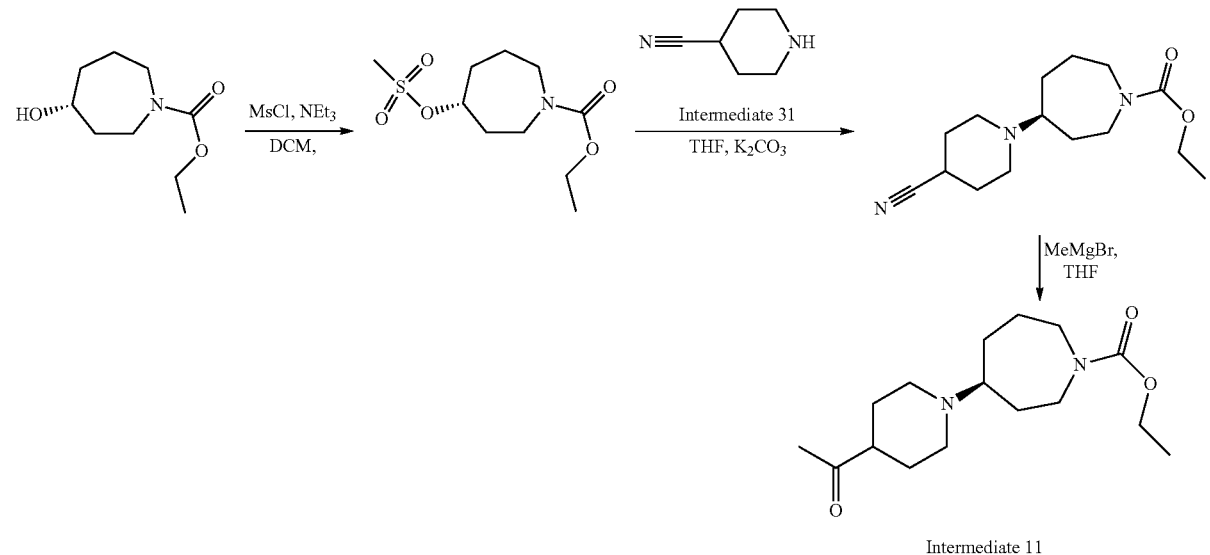

Intermediate 11

Ethyl (4R)-4-hydroxyazepane-1-carboxylate (2.0 g, 10.7 mmol) and triethylamine (3.0 mL, 21.2 mmol) were dissolved in DCM (20 mL) at 0° C., and to the solution was added methanesulfonyl chloride (1.2 mL, 16.0 mmol) dropwise and the resulting reaction mixture stirred at 25° C. for 2 h. The mixture was partitioned between H$_2$O (150 mL) and EtOAc (80 mL), the aqueous layer further extracted with EtOAc (2×80 mL) and combined organics dried (Na$_2$SO$_4$) and solvents removed in vacuo. The residue was purified by column chromatography (normal silica, mesh size: 60-120, 0 to 0.5% MeOH in DCM) to give ethyl (4R)-4-[(methylsulfonyl)oxy]azepane-1-carboxylate (2.5 g, 84%) as a yellow liquid.

LCMS (Method D): m/z 266 (M+H)$^+$ (ES$^+$) at 5.18 min, UV active

Piperidine-4-carbonitrile (1.0 g, 9.1 mmol) was dissolved in THF (20 mL) before addition of K$_2$CO$_3$ (3.8 g, 27.3 mmol). The resulting reaction mixture was cooled to 0° C. and ethyl (4R)-4-[(methylsulfonyl)oxy]azepane-1-carboxylate (2.0 g, 7.5 mmol) added dropwise. The resulting reaction mixture was stirred at 80° C. for 50 h. The solvents were removed in vacuo, the residue partitioned between H$_2$O (200 mL) and EtOAc (110 mL) and the aqueous layer further extracted with EtOAc (2×110 mL). Combined organics were dried (Na$_2$SO$_4$) and the residue purified by column chromatography (normal silica, mesh size: 60-120, 4 to 8% MeOH in DCM) to give ethyl (4S)-4-(4-cyanopiperidin-1-yl) azepane-1-carboxylate (1.6 g, 76%) as a yellow gum.

LCMS (Method C): m/z 280 (M+H)$^+$ (ES$^+$) at 1.49 min, UV active

Ethyl (4S)-4-(4-cyanopiperidin-1-yl)azepane-1-carboxylate (400 mg, 1.4 mmol) was dissolved in THF (10 mL) and reaction mixture stirred at 0° C. for 30 min. Methyl magnesium bromide (3 M sol in ether) (2.0 mL, 5.9 mmol) was added dropwise and the resulting reaction mixture was stirred at 25° C. for 4 h. The solvents were removed in vacuo and the residue partitioned between H$_2$O (60 mL) and EtOAc (40 mL). The aqueous layer was further extracted with EtOAc (2×40 mL), and combined organics dried (Na$_2$SO$_4$) and the residue purified by column chromatography (normal silica, mesh size: 60-120, 2 to 5% MeOH in DCM) to give ethyl (4S)-4-(4-acetylpiperidin-1-yl)azepane-1-carboxylate, intermediate 11 (300 mg, 71%) as a colourless gum.

The data for the title compound are in Table 2.

Route 4

Typical Procedure for the Preparation of Ketones, as Exemplified by the Preparation of Intermediate 16, Ethyl 2-(4-Acetylpiperidin-1-Yl)-6-Azaspiro[3.4]Octane-6-Carboxylate LCMS (Method D): m/z 126 (M+H)$^+$ (ES$^+$) at 3.37 min, UV active To 6-azaspiro[3.4]octan-2-one.TFA (1.0 g, 8.0 mmol) and triethylamine (2.8 mL, 20.0 mmol) in DCM (10 mL) at 0° C. was added ethyl chloroformate (1.1 mL, 12.0 mmol) dropwise and the resulting reaction mixture stirred at 25° C. for 3 h. The mixture was then partitioned between H$_2$O (80 mL) and EtOAc (50 mL), the aqueous layer further extracted with EtOAc (2×50 mL) and combined organics dried (Na$_2$SO$_4$). The solvents were removed in vacuo and the crude residue purified by column chromatography (normal silica, mesh size: 60-120, 0 to 0.5% MeOH in DCM) to give ethyl 2-oxo-6-azaspiro[3.4]octane-6-carboxylate (1.40 g, 89%) as an off white solid.

LCMS (Method C): m/z 198 (M+H)$^+$ (ES$^+$) at 1.75 min, UV active

Ethyl 2-oxo-6-azaspiro[3.4]octane-6-carboxylate (1.00 g, 5.1 mmol), piperidine-4-carbonitrile (0.61 g, 5.6 mmol), ZnCl$_2$ (0.21 g, 0.2 mmol) and triethylamine (3.6 mL, 25.3 mmol) were dissolved in MeOH (15 mL) and the reaction mixture stirred at 50° C. for 1 h. The mixture was then cooled to 0° C. and NaBH$_3$CN (1.30 g, 20.3 mmol) added portionwise before further stirring at 50° C. for 7 h. The solvents were then removed in vacuo, and the resulting residue partitioned between H$_2$O (100 mL) and EtOAc (60 mL). The aqueous layer was extracted with EtOAc (2×60 mL), and combined organics dried over Na$_2$SO$_4$. The residue was purified by column chromatography (normal silica, mesh size: 60-120, 0.5 to 4.0% MeOH in DCM) to give ethyl 2-(4-cyanopiperidin-1-yl)-6-azaspiro[3.4]octane-6-carboxylate (1.40 g, 81%) as a yellow gum.

LCMS (Method C): m/z 293 (M+H)$^+$ (ES$^+$) at 1.53 min, UV active

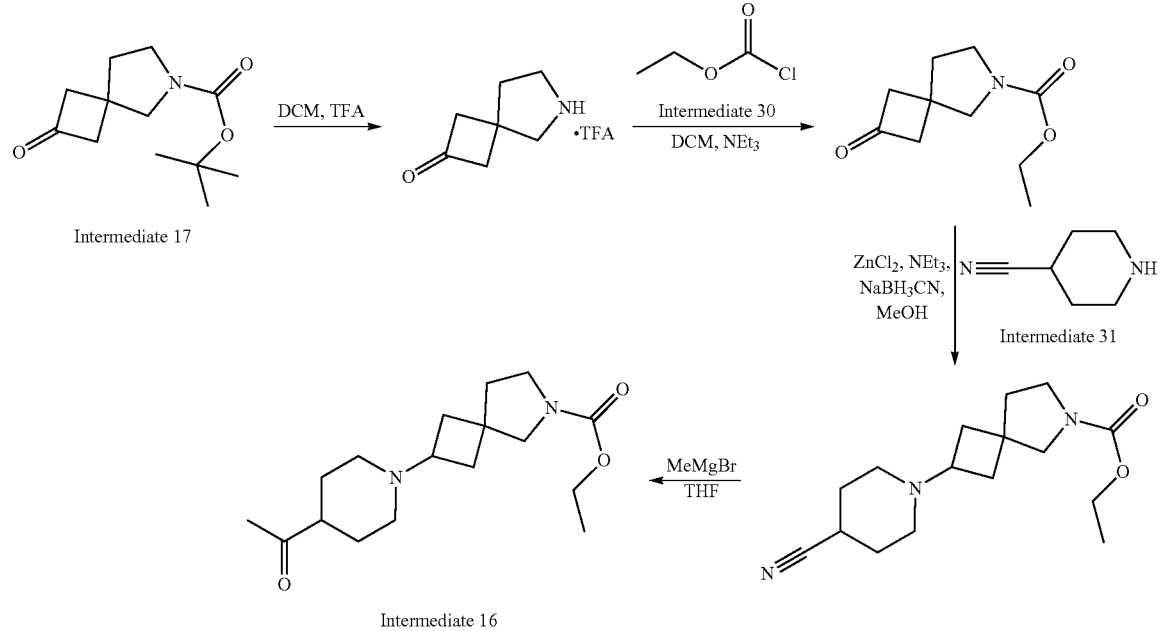

Tert-butyl-2-oxo-6-azaspiro[3.4]octane-6-carboxylate (1.0 g, 4.4 mmol) was dissolved in DCM (10 mL) and trifluoroacetic acid (0.7 mL, 8.9 mmol) was added dropwise. The resulting mixture was stirred at 30° C. for 16 h and the solvents removed in vacuo. The residue was purified by trituration with ether (3×5 mL) to give 6-azaspiro[3.4]octan-2-one.TFA (600 mg, 56%) as an off white solid.

Ethyl 2-(4-cyanopiperidin-1-yl)-6-azaspiro[3.4]octane-6-carboxylate (200 mg, 0.69 mmol) was dissolved in THF (5 mL) and the reaction mixture stirred at 0° C. for 30 min. Methyl magnesium bromide (1.4 M sol in ether) (2.0 mL, 2.85 mmol) was then added dropwise and the resulting reaction mixture stirred at 25° C. for 4 h. The solvent was removed in vacuo and the residue partitioned between H$_2$O (40 mL) and EtOAc (25 mL). The aqueous layer was extracted with EtOAc (2×25 mL) and combined organics were dried over Na$_2$SO$_4$. The residue was purified by column chromatography (normal silica, mesh size: 60-120, 1.0 to 3.0% MeOH in DCM) to give ethyl 2-(4-acetylpiperidin-1-yl)-6-azaspiro[3.4]octane-6-carboxylate (150 mg, 71%) as a yellow gum.

The data for the title compound are in Table 2.

Route 5

Procedure for the Preparation of Carboxylic Acid Intermediate 21, 1-[1-(Ethoxycarbonyl)Azepan-4-Yl]Piperidine-4-Carboxylic Acid Ethyl 4-(4-(ethoxycarbonyl)piperidin-1-yl)-azepane-1-carboxylate (2.3 g, 7.0 mmol), LiOH (0.34 g, 14.1 mmol) and H$_2$O (15 mL) were dissolved in THF (15 mL) and the resulting reaction mixture stirred at 80° C. for 16 h. The solvents were removed in vacuo and the residue partitioned between H$_2$O (80 mL) and EtOAc (50 mL). The aqueous layer was extracted with EtOAc (2×50 mL) and combined organics dried over Na$_2$SO$_4$. The crude residue was purified by column chromatography (normal silica, mesh size: 60-120, 6 to 10% MeOH in DCM) to give 1-(1-(ethoxycarbonyl)azepan-4-yl)piperidine-4-carboxylic acid, intermediate 21 (1.4 g, 70%) as a white solid.

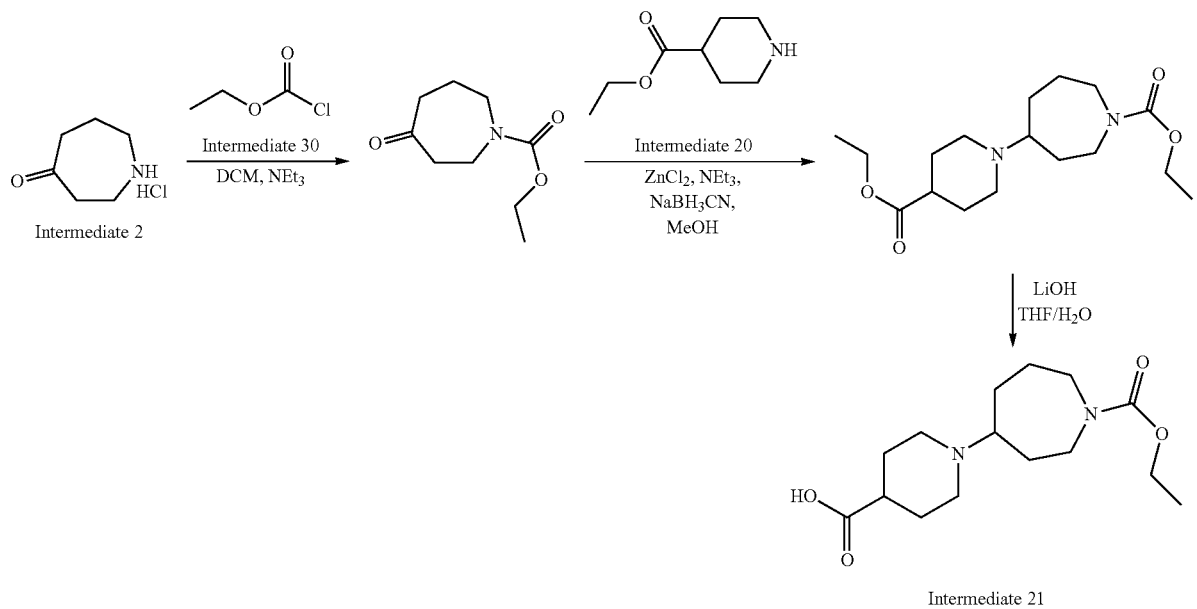

Azepan-4-one.HCl (5.0 g, 44 mmol) and triethylamine (19.0 mL, 133 mmol) were dissolved in DCM (60 mL) at 0° C. followed by dropwise addition of ethyl chloroformate (6.3 mL, 66 mmol). The resulting reaction mixture was stirred at 25° C. for 3 h and the mixture partitioned between H$_2$O (200 mL) and EtOAc (70 mL). The aqueous layer was further extracted with EtOAc (2×70 mL) and combined organics dried (Na$_2$SO$_4$) and solvents removed in vacuo. The crude compound was purified by column chromatography (normal silica, mesh size: 60-120, 0 to 0.5% MeOH in DCM) to give ethyl 4-oxoazepane-1-carboxylate (7.8 g, 95%) as a brown gum.

LCMS (Method C): m/z 186 (M+H)$^+$ (ES$^+$) at 0.87 min, UV active

Ethyl 4-oxoazepane-1-carboxylate (3.0 g, 16.2 mmol), ethyl piperidine-4-carboxylate (2.5 g, 16.2 mmol) and triethylamine (8.1 g, 81.0 mmol) were dissolved in MeOH (50 mL) and the reaction mixture degassed with nitrogen for 30 min. ZnCl$_2$ (110 mg, 0.8 mmol) was added and the mixture stirred at 60° C. for 3 h. The reaction mixture was cooled to 0° C., NaCNBH$_3$ (5.1 g, 81.0 mmol) was added portionwise and the mixture stirred at rt for 8 h. The mixture was diluted with water (500 mL), extracted with DCM (3×150 mL) and combined organics dried over Na$_2$SO$_4$ and concentrated in vacuo. The crude product was purified by column chromatography (normal phase, neutral silica gel, 60-120 mesh, 0 to 1% MeOH in DCM) to give ethyl 4-(4-(ethoxycarbonyl)piperidin-1-yl)azepane-1-carboxylate (2.5 g, 47%) as a yellow gum.

LCMS (Method F): m/z 328 (M+H)$^+$ (ES$^+$) at 2.52 min, UV active

The data for the title compound are in Table 2.

General Synthetic Procedures

Route a

Typical Procedure for the Preparation of Oximes, as Exemplified by the Preparation of Example 1-1, Ethyl 4-{4-[N-Methoxyethanimidoyl]Piperidin-1-Yl}Azepane-1-Carboxylate

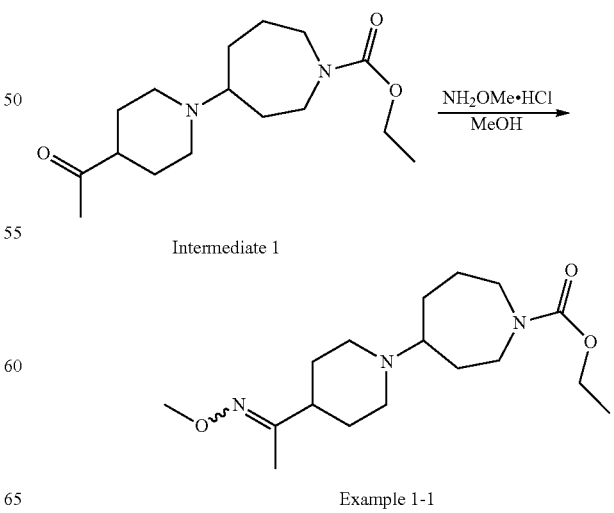

To a solution of ethyl 4-(4-acetylpiperidin-1-yl)azepane-1-carboxylate (200 mg, 0.68 mmol) in MeOH (5 mL) was added O-methyl hydroxylamine hydrochloride (85 mg, 1.01 mmol) and sodium acetate (83 mg, 1.01 mmol) at rt and the resulting reaction mixture stirred for 8 h. The solvent was removed in vacuo, the residue partitioned between H₂O (50 mL) and EtOAc (30 mL) and the aqueous layer further extracted with EtOAc (2×30 mL). Combined organics were dried (Na₂SO₄) and the solvent removed in vacuo. The crude compound was purified by Prep HPLC [reverse phase HPLC (X-Bridge, C-18, 250×19 mm, 5 μm, 19 mL per min, gradient 40 to 45% (over 15 min), 100% (over 2.0 min) then 40% (over 4.0 min), 0.1% NH₃ in MeCN/water] to give ethyl 4-{4-[N-methoxyethanimidoyl]piperidin-1-yl}azepane-1-carboxylate Isomer-1, (5 mg, 2.3%) as a colourless gum and Isomer-2, (25 mg, 11.0%) as a colourless gum.

The data for the title compound are in Table 3.

Route b

Procedure for the Preparation of Example 3-1, Ethyl 4-{4-[N'-Methoxy-N-(2-Methylpropyl)Carbamimidoyl]Piperidin-1-Yl}Azepane-1-Carboxylate Ethyl 4-[4-(methoxycarbamoyl)piperidin-1-yl]azepane-1-carboxylate (250 mg, 0.76 mmol) was dissolved in MeOH and thionyl chloride (135 mg, 1.14 mmol) added at 0° C. The mixture was then stirred at rt for 3 h, cooled to 0° C. and basified with a saturated solution of NaHCO₃. The mixture was diluted with water (60 mL), extracted with DCM (3×20 mL) and combined organics dried over Na₂SO₄ and concentrated in vacuo. The crude product was purified by column chromatography (normal phase, neutral silica gel, 60-120 mesh, 0 to 2.5% MeOH in DCM) to give ethyl 4-{4-[chloro(methoxyimino)methyl]piperidin-1-yl}azepane-1-carboxylate (100 mg, 38%) as a yellow gum.

LCMS (Method C): m/z 346 (M+H)⁺ (ES⁺) at 1.70 min, UV active

Ethyl 4-{4-[(E)-chloro(methoxyimino)methyl]piperidin-1-yl}azepane-1-carboxylate, K₂CO₃ and 2-methylpropan-1-amine were dissolved in DMF and the mixture allowed to stir at 90° C. for 3 h. The reaction mixture was then diluted

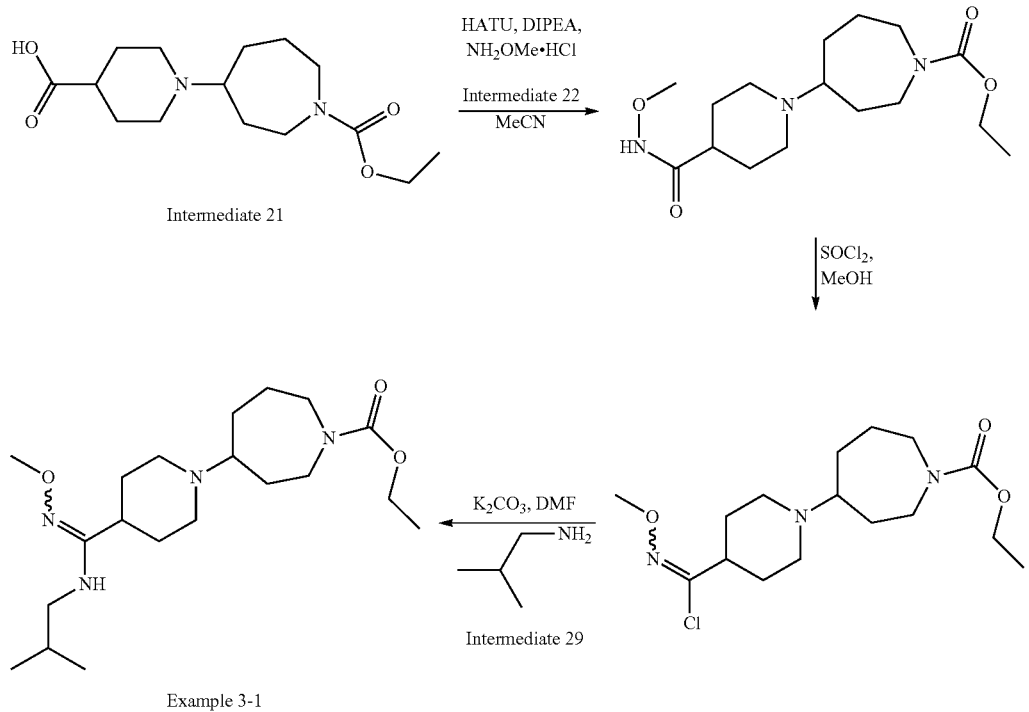

Intermediate 21

Example 3-1

1-(1-(Ethoxycarbonyl)azepan-4-yl)piperidine-4-carboxylic acid (1.0 g, 33.5 mmol) and HATU (1.4 g, 36.8 mmol) were dissolved in MeCN (20 mL) and the reaction stirred at rt for 15 min. O-methyl hydroxylamine hydrochloride (308 mg, 36.8 mmol) and DIPEA (1.27 g, 99.5 mmol) were added and the mixture further stirred at rt for 4 h. The mixture was quenched with water (150 mL), extracted with DCM (3×60 mL) and combined organics dried over Na₂SO₄ and concentrated in vacuo. The crude residue was purified by column chromatography (normal phase, neutral silica gel, 60-120 mesh, 0 to 8% MeOH in DCM) to give ethyl 4-[4-(methoxycarbamoyl)piperidin-1-yl]azepane-1-carboxylate (400 mg, 36%) as a yellow gum.

LCMS (Method C): m/z 328 (M+H)⁺ (ES⁺) at 1.47 min, UV active with water (60 mL), extracted with DCM (3×20 mL) and combined organics dried over Na₂SO₄ and concentrated in vacuo. The crude product was purified by column chromatography (normal phase, neutral silica gel, 60-120 mesh, 0 to 4% MeOH in DCM) to give ethyl 4-{4-[N'-methoxy-N-(2-methylpropyl)carbamimidoyl]piperidin-1-yl}azepane-1-carboxylate, example 3-1 (25 mg, 32%) as a brown gum.

The data for the title compound are in Table 3.

Route c

Procedure for the Preparation of Example 4-1, Ethyl 4-(4-{Cyano[(Propan-2-Yloxy)Imino]Methyl}Piperidin-1-Yl)Azepane-1-Carboxylate

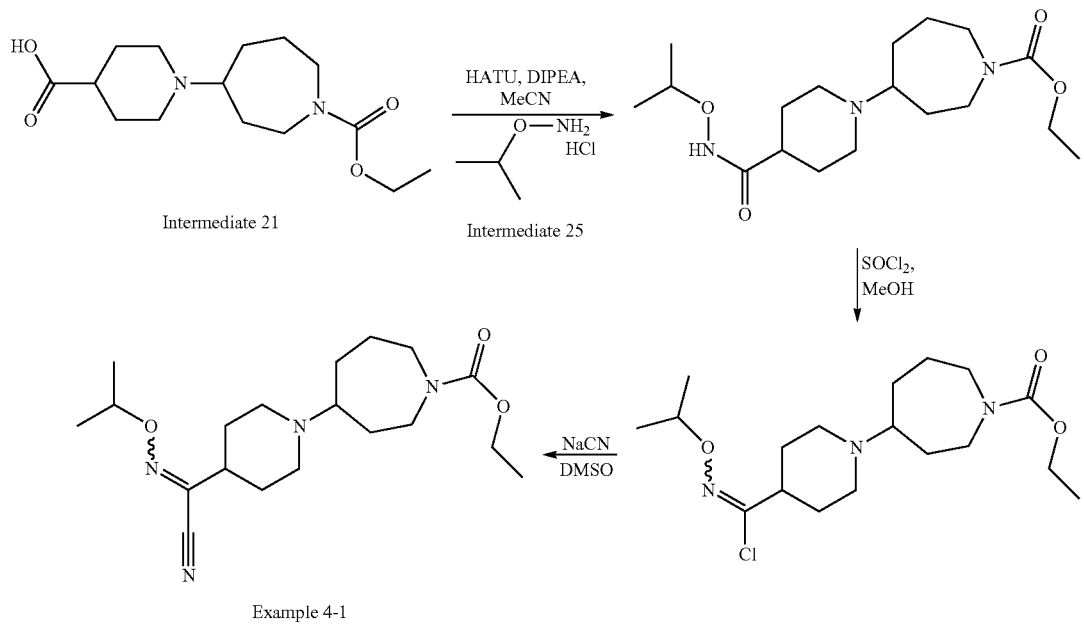

Example 4-1

To a solution of 1-(1-(ethoxycarbonyl)azepan-4-yl)piperidine-4-carboxylic acid (0.72 g, 2.41 mmol) in DMF (10 mL) was added HATU (1.37 g, 3.61 mmol), O-isopropylhydroxylamine.HCl (0.30 g, 2.65 mmol) and DIPEA (1.26 mL, 7.23 mmol) and the resulting mixture stirred at rt for 65 h. The solvent was removed in vacuo and the residue diluted with DCM and washed with NaHCO$_3$ and brine. Organics were dried over MgSO$_4$ and concentrated in vacuo. The residue was purified on silica (25 g SNAP cartridge, 0-9% MeOH in DCM) to yield the desired product ethyl 4-{4-[(propan-2-yloxy)carbamoyl]piperidin-1-yl}azepane-1-carboxylate (101 mg, 12%) as a yellow gum.

LCMS (Method B): m/z 356 (M+H)$^+$ (ES$^+$) at 2.58 min, UV inactive.

To a solution of ethyl 4-{4-[(propan-2-yloxy)carbamoyl]piperidin-1-yl}azepane-1-carboxylate (96 mg, 0.27 mmol) in anhydrous 1,2-dichloroethane (10 mL) was added phosphorus oxychloride (45 mg, 0.29 mmol) and the mixture heated to 85° C. for 16 h. The mixture was then allowed to cool to rt before quenching with ice. The mixture was then diluted with sat. aq. NaHCO$_3$ and extracted with DCM (2×20 mL). Combined organics were dried over MgSO$_4$, filtered and concentrated in vacuo to yield ethyl 4-(4-{chloro[(propan-2-yloxy)imino]methyl}piperidin-1-yl)azepane-1-carboxylate (99 mg, 100%) as an amber gum, which was taken on directly to the next step.

To a stirred solution of ethyl 4-(4-{chloro[(propan-2-yloxy)imino]methyl}piperidin-1-yl)azepane-1-carboxylate (99 mg, 0.27 mmol) in anhydrous DMSO (2 mL) was added sodium cyanide (26 mg, 0.54 mmol) and the solution heated to 95° C. under N$_2$ for 7 h before addition of further sodium cyanide (26 mg, 0.54 mmol) and heating at 95° C. for 48 h. A further portion of sodium cyanide (26 mg, 0.54 mmol) was then added and the mixture heated to 110° C. for 16 h. The mixture was then allowed to cool to rt and concentrated in vacuo. The residue was diluted with DCM and washed with 5% potassium carbonate (aq.) (20 mL×1) and brine (20 mL×1). The organic layer was dried over MgSO$_4$, filtered and concentrated in vacuo. The residue was purified on silica (0-5% MeOH in DCM) to yield ethyl 4-(4-{cyano[(propan-2-yloxy)imino]methyl}piperidin-1-yl)azepane-1-carboxylate, example 4-1 (5.0 mg, 5%) as a colourless oil.

The data for the title compound are in Table 3.

TABLE 2

Starting Materials and Intermediates

| Intermediate | Route | Name | Data |
|---|---|---|---|
| 1 | Route 1 and intermediate 2 | Ethyl 4-(4-acetylpiperidin-1-yl)azepane-1-carboxylate | LCMS (Method C): m/z 297 (M + H)+ (ES+), at 1.48 min, UV active |
| 2 | | 4-Azepanone. HCl | Commercially available, CAS: 50492-22-3 |
| 3 | Route 1 and intermediates 2 and 7 | Ethyl 4-(4-propanoylpiperidin-1-yl)azepane-1-carboxylate | LCMS (Method F): m/z 311 (M + H)+ (ES+), at 0.48 min, UV active |
| 4 | Route 1 and intermediates 2 and 8 | Ethyl 4-(4-butanoylpiperidin-1-yl)azepane-1-carboxylate | LCMS (Method D): m/z 325 (M + H)+ (ES+), at 6.27 min, UV active |
| 5 | Route 1 and intermediates 2 and 9 | Ethyl 4-[4-(2-methylpropanoyl)piperidin-1-yl]azepane-1-carboxylate | LCMS (Method F): m/z 325 (M + H)+ (ES+), at 1.66 min, UV active |

TABLE 2-continued

Starting Materials and Intermediates

| Intermediate | Route | Name | Data |
|---|---|---|---|
| 6 | Route 1 and 2 and intermediates 2 and 10 | Ethyl 4-[4-(4-methylpentanoyl)piperidin-1-yl]azepane-1-carboxylate | LCMS (Method D): m/z 353 (M + H)+ (ES+), at 7.21 min, UV active |
| 7 | | Ethyl magnesium bromide | Commercially available, CAS: 925-90-6 |
| 8 | | Propyl magnesium bromide | Commercially available, CAS: 927-77-5 |
| 9 | | Isopropyl magnesium bromide | Commercially available, CAS: 920-39-8 |
| 10 | | 1-Bromo-3-methylbutane | Commercially available, CAS: 107-82-4 |
| 11 | Route 3 and intermediate 12 | Ethyl (4S)-4-(4-acetylpiperidin-1-yl)azepane-1-carboxylate | LCMS (Method C): m/z 297 (M + H)+ (ES+), at 1.51 min, UV active |
| 12 | | Ethyl (4R)-4-hydroxyazepane-1-carboxylate | 1H NMR (400 MHz, CDCl3) δ: 1.26 (t, 3 H), 1.50 (bs, 1 H), 1.62-2.05 (m, 6 H), 3.28-3.52 (m, 4 H), 3.89 (m, 1 H), 4.13 (m, 2 H) |
| 13 | Route 3 and intermediates 7 and 12 | Ethyl (4S)-4-(4-propanoylpiperidin-1-yl)azepane-1-carboxylate | LCMS (Method D): m/z 311 (M + H)+ (ES+), at 5.81 min, UV active |
| 14 | Route 3 and intermediates 8 and 12 | Ethyl (4S)-4-(4-butanoylpiperidin-1-yl)azepane-1-carboxylate | LCMS (Method C): m/z 325 (M + H)+ (ES+), at 1.69 min, UV active |
| 15 | Route 3 and intermediates 9 and 12 | Ethyl (4S)-4-[4-(2-methylpropanoyl)piperidin-1-yl]azepane-1-carboxylate | LCMS (Method C): m/z 325 (M + H)+ (ES+), at 1.59 min, UV active |
| 16 | Route 4 and intermediate 17 | Ethyl 2-(4-acetylpiperidin-1-yl)-6-azaspiro[3.4]octane-6-carboxylate | LCMS (Method C): m/z 310 (M + H)+ (ES+), at 1.59 min, UV active |
| 17 | | Tert-butyl 2-oxo-6-azaspiro[3.4]octane-6-carboxylate | Commercially available, CAS: 203661-71-6 |
| 18 | Route 4 and intermediates 17 and 7 | Ethyl 2-(4-propanoylpiperidin-1-yl)-6-azaspiro[3.4]octane-6-carboxylate | LCMS (Method C): m/z 323 (M + H)+ (ES+), at 1.62 min, UV active |
| 19 | Route 4 and intermediates 17 and 8 | Ethyl 2-(4-butanoylpiperidin-1-yl)-6-azaspiro[3.4]octane-6-carboxylate | m/z 338 (M + H)+ (ES+) |
| 20 | | Ethyl piperidine-4-carboxylate | Commercially available, CAS: 1126-09-6 |
| 21 | Route 5 and intermediates 20 and 2 | 1-[1-(Ethoxycarbonyl)azepan-4-yl]piperidine-4-carboxylic acid | LCMS (Method C): m/z 299 (M + H)+ (ES+), at 1.45 min, UV active |
| 22 | | O-Methyl hydroxylamine hydrochloride | Commercially available, CAS: 593-56-6 |
| 23 | | O-Ethylhydroxylamine hydrochloride | Commercially available, CAS: 3332-29-4 |
| 24 | | O-Propylhydroxylamine hydrochloride | Commercially available, CAS: 6084-54-4 |
| 25 | | O-Isopropylhydroxylamine hydrochloride | Commercially available, CAS: 4490-81-7 |
| 29 | | 2-Methylpropan-1-amine | Commercially available, CAS: 78-81-9 |
| 30 | | Ethyl chloroformate | Commercially available, CAS: 541-41-3 |
| 31 | | Piperidine-4-carbonitrile | Commercially available, CAS: 4395-98-6 |
| 32 | | Methyl magnesium bromide | Commercially available, CAS: 75-16-1 |

TABLE 3

| Ex. No. | Name | Intermediates | Synthetic method | 1H NMR | LCMS Method | LCMS data |
|---|---|---|---|---|---|---|
| 1-1 | Isomer 1 (racemic): Ethyl 4-{4-[N-methoxy-ethanimidoyl]piperidin-1-yl}azepane-1-carboxylate | 1 | a | 400 MHz, (MeOD-d4) δ: 1.26-1.31 (m, 7 H), 1.47-1.72 (m, 8 H), 1.81 (s, 3 H), 1.93-2.12 (m, 4 H), 2.90-3.17 (m, 2 H), 3.56-3.67 (m, 2 H), 3.78 (s, 3 H), 4.11-4.17 (m, 2 H) | E | m/z 326 (M + H)+ (ES+) at 5.93 min, UV active |

TABLE 3-continued

| Ex. No. | Name | Intermediates | Synthetic method | $^1$H NMR | LCMS Method | LCMS data |
|---|---|---|---|---|---|---|
| 1-1 | Isomer 2 (racemic): Ethyl 4-{4-[N-methoxy-ethanimidoyl]piperidin-1-yl}azepane-1-carboxylate | 1 | a | 400 MHz, (DMSO-d$_6$) δ: 1.17 (td, J = 7.0, 2.0 Hz, 3 H), 1.33-1.84 (m, 13 H), 1.99-2.23 (m, 3 H), 2.32-2.44 (m, 1 H), 2.66-2.80 (m, 2 H), 3.16-3.27 (m, 2 H), 3.39-3.49 (m, 2 H), 3.71 (s, 3 H), 4.03 (qd, J = 7.0, 2.5 Hz, 2 H) | E | m/z 326 (M + H)$^+$ (ES$^+$) at 6.22 min, UV active |
| (S)-1-1 | Isomer 1: Ethyl (4S)-4-{4-[N-methoxy-ethanimidoyl]piperidin-1-yl}azepane-1-carboxylate | 11 | a | 400 MHz, (DMSO-d$_6$) δ: 1.17 (td, J = 7.0, 2.0 Hz, 3 H), 1.28-1.63 (m, 7 H), 1.71 (s, 3 H), 1.74-1.89 (m, 3 H), 2.03-2.47 (m, 2 H), 2.60-2.98 (m, 4 H), 3.17-3.24 (m, 2 H), 3.41-3.52 (m, 2 H), 3.70 (s, 3 H), 4.03 (qd, J = 7.0, 3.0 Hz, 2 H) | D | m/z 326 (M + H)$^+$ (ES$^+$) at 5.99 min, UV active |
| (S)-1-1 | Isomer 2: Ethyl (4S)-4-{4-[N-methoxy-ethanimidoyl]piperidin-1-yl}azepane-1-carboxylate | 11 | a | 400 MHz, (DMSO-d$_6$) δ: 1.17 (td, J = 7.0, 2.0 Hz, 3 H), 1.34-1.63 (m, 7 H), 1.72 (s, 3 H), 1.73-1.86 (m, 3 H), 1.99-2.20 (m, 3 H), 2.32-2.45 (m, 1 H), 2.66-2.81 (m, 2 H), 3.16-3.25 (m, 2 H), 3.41-3.49 (m, 2 H), 3.71 (s, 3 H), 4.03 (qd, J = 7.0, 2.5 Hz, 2 H) | D | m/z 326 (M + H)$^+$ (ES$^+$) at 6.29 min, UV active |
| 1-2 | Isomer 1 (racemic): Ethyl 4-{4-[N-methoxy-propanimidoyl]piperidin-1-yl}azepane-1-carboxylate | 3 | a | 400 MHz, (DMSO-d$_6$) δ: 0.99 (t, J = 7.5 Hz, 3 H), 1.16-1.18 (m 3 H), 1.28-1.62 (m, 7 H), 1.70-1.85 (m, 3 H), 2.09-2.23 (m, 4 H), 2.32-2.43 (m, 1 H), 2.65-2.90 (m, 3 H), 3.14-3.28 (m, 2 H), 3.39-3.50 (m, 2 H), 3.71 (s, 3 H), 4.00-4.05 (m, 2 H) | E | m/z 340 (M + H)$^+$ (ES$^+$) at 6.77 min, UV active |
| 1-2 | Isomer 2 (racemic): Ethyl 4-{4-[N-methoxy-propanimidoyl]piperidin-1-yl}azepane-1-carboxylate | 3 | a | 400 MHz, (DMSO-d$_6$) δ: 0.98 (t, J = 7.5 Hz, 3 H), 1.17 (td, J = 7.0, 2.0 Hz, 3 H), 1.34-1.86 (m, 10 H), 2.03-2.21 (m, 5 H), 2.39-2.43 (m, 1 H), 2.69-2.82 (m, 2 H), 3.16-3.25 (m, 2 H), 3.39-3.52 (m, 2 H), 3.70 (s, 3 H), 4.03 (qd, J = 7.0, 2.5 Hz, 2 H) | G | m/z 340 (M + H)$^+$ (ES$^+$) at 4.44 min, UV active |
| (S)-1-2 | Isomer 1: Ethyl (4S)-4-{4-[N-methoxy-propanimidoyl]piperidin-1-yl}azepane-1-carboxylate | 13 | a | 400 MHz, (DMSO-d$_6$) δ: 0.99 (t, J = 7.0 Hz, 3 H), 1.17 (t, J = 6.0 Hz, 3 H), 1.25-1.65 (m, 7 H), 1.67-1.87 (m, 3 H), 2.11-2.27 (m, 4 H), 2.31-2.43 (m, 1 H), 2.65-2.91 (m, 3 H), 3.13-3.27 (m, 2 H), 3.39-3.51 (m, 2 H), 3.72 (s, 3 H), 3.98-4.09 (m, 2 H) | C | m/z 340 (M + H)$^+$ (ES$^+$) at 1.69 min, UV active |
| (S)-1-2 | Isomer 2: Ethyl (4S)-4-{4-[N-methoxy-propanimidoyl]piperidin-1-yl}azepane-1-carboxylate | 13 | a | 400 MHz, (DMSO-d$_6$) δ: 0.98 (t, J = 7.5 Hz, 3 H), 1.17 (td, J = 7.0, 2.0 Hz, 3 H), 1.29-1.89 (m, 10 H), 2.01-2.21 (m, 5 H), 2.34-2.44 (m, 1 H), 2.66-2.80 (m, 2 H), 3.16-3.28 (m, 2 H), 3.39-3.49 (m, 2 H), 3.71 (s, 3 H), 4.03 (qd, J = 7.0, 2.0 Hz, 2 H) | C | m/z 340 (M + H)$^+$ (ES$^+$) at 1.74 min, UV active |
| 1-3 | Isomer 1 (racemic): Ethyl 4-{4-[N-methoxybutan-imidoyl]piperidin-1-yl}azepane-1-carboxylate | 4 | a | 400 MHz, (DMSO-d$_6$) δ: 0.88 (t, J = 7.5 Hz, 3 H), 1.17 (td, J = 7.0, 2.0 Hz, 3 H), 1.30-1.63 (m, 9 H), 1.70-1.87 (m, 3 H), 2.07 (t, J = 7.5 Hz, 2 H), 2.11-2.24 (m, 2 H), 2.70-2.89 (m, 3 H), 3.12-3.27 (m, 2 H), 3.40-3.54 (m, 3 H), 3.71 (s, 3 H), 4.03 (qd, J = 7.0, 2.5 Hz, 2 H) | C | m/z 354 (M + H)$^+$ (ES$^+$) at 1.77 min, UV active |
| 1-3 | Isomer 2 (racemic): Ethyl 4-{4-[N-methoxy-butanimidoyl]piperidin-1-yl}azepane-1-carboxylate | 4 | a | 400 MHz, (DMSO-d$_6$) δ: 0.87 (t, J = 7.5 Hz, 3 H), 1.17 (td, J = 7.0, 2.0 Hz, 3 H), 1.27-1.88 (m, 13 H), 1.96-2.28 (m, 4 H), 2.32-2.45 (m, 1 H), 2.66-2.86 (m, 2 H), 3.16-3.25 (m, 2 H), 3.41-3.52 (m, 2 H), 3.70 (s, 3 H), 4.03 (qd, J = 7.0, 2.5 Hz, 2 H) | C | m/z 354 (M + H)$^+$ (ES$^+$) at 1.82 min, UV active |
| (S)-1-3 | Isomer 1: Ethyl (4S)-4-{4-[N-methoxy-butanimidoyl]piperidin-1-yl}azepane-1-carboxylate | 14 | a | 400 MHz, (MeOD-d$_4$) δ: 0.96 (t, J = 7.5 Hz, 3 H), 1.26-1.31 (m, 4 H), 1.44-1.77 (m, 8 H), 1.91-2.18 (m, 6 H), 2.35-2.51 (m, 2 H), 2.55-2.65 (m, 1 H), 2.85-3.04 (m, 3 H), 3.36-3.40 (m, 1 H), 3.54-3.61 (m, 2 H), 3.79 (s, 3 H), 4.11-4.17 (m, 2 H) | D | m/z 354 (M + H)$^+$ (ES$^+$) at 7.45 min, UV active |
| (S)-1-3 | Isomer 2: Ethyl (4S)-4-{4-[N-methoxy-butanimidoyl]piperidin-1-yl}azepane-1-carboxylate | 14 | a | 400 MHz, (MeOD-d$_4$) δ: 0.95 (t, J = 7.5 Hz, 3 H), 1.26-1.31 (m, 4 H), 1.48-1.81 (m, 9 H), 1.91-2.26 (m, 6 H), 2.37-2.46 (m, 2 H), 2.57-2.62 (m, 1 H), 2.87-2.97 (m, 2 H), 3.36-3.41 (m, 1 H), 3.54-3.62 (m, 2 H), 3.77 (s, 3 H), 4.11-4.17 (m, 2 H) | D | m/z 354 (M + H)$^+$ (ES$^+$) at 7.61 min, UV active |
| 1-4 | Isomer 1 (racemic): Ethyl 4-{4-[N-methoxy-2-methylpropan-imidoyl]piperidin-1-yl}azepane-1-carboxylate | 5 | a | 400 MHz, (MeOD-d$_4$) δ: 1.12 (d, J = 7.0 Hz, 6 H), 1.26-1.31 (m, 5 H), 1.46-1.78 (m, 6 H), 1.87-2.61 (m, 6 H), 2.83-2.94 (m, 2 H), 3.05-3.12 (m, 1 H), 3.24 (q, J = 7.0 Hz, 2 H), 3.54-3.62 (m, 2 H), 3.76 (s, 3 H), 4.11-4.17 (m, 2 H) | C | m/z 354 (M + H)$^+$ (ES$^+$) at 1.79 min, UV active |
| 1-4 | Isomer 2 (racemic): Ethyl 4-{4-[N-methoxy-2-methylpropan-imidoyl]piperidin-1-yl}azepane-1-carboxylate | 5 | a | 400 MHz, (DMSO-d$_6$) δ: 1.03 (d, J = 7.0 Hz, 6 H), 1.11 (t, J = 7.0 Hz, 2 H), 1.17 (td, J = 7.0, 2.5 Hz, 3 H), 1.32-1.85 (m, 7 H), 2.06-2.20 (m, 3 H), 2.37-2.41 (m, 1 H), 2.66-2.78 (m, 2 H), 2.93-3.06 (m, 2 H), 3.17-3.25 (m, 2 H), 3.39-3.44 (m, 2 H), 3.69 (s, 3 H), 4.03 (qd, J = 7.0, 3.0 Hz, 2 H) | G | m/z 354 (M + H)$^+$ (ES$^+$) at 4.84 min, UV active |
| 1-5 | Isomer 1 (racemic): Ethyl 4-{4-[N-methoxy-2-methylpropan-imidoyl]piperidin-1-yl}azepane-1-carboxylate | 15 | a | 400 MHz, (MeOD-d$_4$) δ: 1.11 (d, J = 6.5 Hz, 6 H), 1.26-1.31 (m, 4 H), 1.43-1.73 (m, 5 H), 1.91-2.06 (m, 5 H), 2.35-2.38 (m, 2 H), 2.52-2.59 (m, 2 H), 2.75-2.90 (m, 3 H), 3.24 (q, J = 7.0 Hz, 1 H), 3.55-3.61 (m, 2 H), 3.77 (s, 3 H), 4.11-4.17 (m, 2 H) | C | m/z 354 (M + H)$^+$ (ES$^+$) at 1.79 min, UV active |
| 1-5 | Isomer 2 (racemic): Ethyl 4-{4-[N-methoxy-2-methylpropan- | 15 | a | 400 MHz, (MeOD-d$_4$) δ: 1.12 (d, J = 7.0 Hz, 6 H), 1.26-1.31 (m, 4 H), 1.47-1.79 (m, 7 H), 1.91-2.06 (m, 3 H), 2.18-2.60 (m, 4 H), 2.85-2.96 (m, 2 H), 3.06-3.13 (m, | C | m/z 354 (M + H)$^+$ (ES$^+$) at 1.86 min, |

TABLE 3-continued

| Ex. No. | Name | Intermediates | Synthetic method | ¹H NMR | LCMS Method | LCMS data |
|---|---|---|---|---|---|---|
| | imidoyl]piperidin-1-yl}azepane-1-carboxylate | | | 1 H), 3.24 (q, J = 7.5 Hz, 1 H), 3.54-3.61 (m, 2 H), 3.76 (s, 3 H), 4.11-4.17 (m, 2 H) | | UV active |
| 1-6 | Isomer 1 (racemic): Ethyl 4-{4-[N-methoxy-4-methylpentan-imidoyl]piperidin-1-yl}azepane-1-carboxylate | 6 | a | 400 MHz, (DMSO-d₆) δ: 0.87 (d, J = 6.5 Hz, 6 H), 1.15-1.86 (m, 16 H), 2.07-2.23 (m, 4 H), 2.36-2.40 (m, 1 H), 2.68-2.89 (m, 3 H), 3.13-3.28 (m, 2 H), 3.40-3.50 (m, 2 H), 3.70 (s, 3 H), 4.03 (qd, J = 7.0, 2.0 Hz, 2 H) | C | m/z 382 (M + H)⁺ (ES⁺) at 1.97 min, UV active |
| 1-6 | Isomer 2 (racemic): Ethyl 4-{4-[N-methoxy-4-methylpentan-imidoyl]piperidin-1-yl}azepane-1-carboxylate | 6 | a | 400 MHz, (DMSO-d₆) δ: 0.87 (d, J = 6.5 Hz, 6 H), 1.15-1.85 (m, 16 H), 2.07-2.21 (m, 4 H), 2.36-2.40 (m, 1 H), 2.68-2.88 (m, 3 H), 3.14-3.27 (m, 2 H), 3.40-3.49 (m, 2 H), 3.70 (s, 3 H), 3.40-4.05 (m, 2 H) | C | m/z 382 (M + H)⁺ (ES⁺) at 2.00 min, UV active |
| 1-7 | Isomer 1 (racemic): Ethyl 4-{4-[N-ethoxy-ethanimidoyl]piperidin-1-yl}azepane-1-carboxylate | 1 and 23 | a | 400 MHz, (DMSO-d₆) δ: 1.13-1.89 (m, 18 H), 2.11-2.26 (m, 2 H), 2.34-2.44 (m, 1 H), 2.68-2.93 (m, 4 H), 3.16-3.24 (m, 2 H), 3.42-3.47 (m, 2 H), 3.95 (q, J = 7.0 Hz, 2 H), 4.03 (qd, J = 7.0, 3.0 Hz, 2 H) | E | m/z 340 (M + H)⁺ (ES⁺) at 6.50 min, UV active |
| 1-7 | Isomer 2 (racemic): Ethyl 4-{4-[N-ethoxy-ethanimidoyl]piperidin-1-yl}azepane-1-carboxylate | 1 and 23 | a | 400 MHz, (DMSO-d₆) δ: 1.14-1.19 (m, 6 H), 1.31-1.85 (m, 13 H), 2.01-2.22 (m, 3 H), 2.32-2.46 (m, 1 H), 2.68-2.74 (m, 2 H), 3.16-3.25 (m, 2 H), 3.41-3.46 (m, 2 H), 3.94-4.06 (m, 4 H) | E | m/z 340 (M + H)⁺ (ES⁺) at 6.60 min, UV active |
| 1-8 | Isomer 1 (racemic): Ethyl 4-{4-[N-propoxy-ethanimidoyl]piperidin-1-yl}azepane-1-carboxylate | 1 and 24 | a | 400 MHz, (DMSO-d₆) δ: 0.84-0.89 (m, 3 H), 1.15-1.19 (td, J = 7.0, 2.0 Hz, 3 H), 1.34-1.87 (m, 15 H), 2.15-2.23 (m, 2 H), 2.33-2.44 (m, 1 H), 2.68-2.91 (m, 3 H), 3.16-3.24 (m, 2 H), 3.41-3.51 (m, 2 H), 3.87 (q, J = 6.5 Hz, 2 H), 4.03 (qd, J = 7.0, 3.0 Hz, 2 H) | E | m/z 354 (M + H)⁺ (ES⁺) at 7.15 min, UV active |
| 1-8 | Isomer 2 (racemic): Ethyl 4-{4-[N-propoxy-ethanimidoyl]piperidin-1-yl}azepane-1-carboxylate | 1 and 24 | a | 400 MHz, (DMSO-d₆) δ: 0.87 (t, J = 7.5 Hz, 3 H), 1.17 (td, J = 7.0, 2.0 Hz, 3 H), 1.34-1.88 (m, 15 H), 1.99-2.07 (m, 1 H), 2.13-2.22 (m, 2 H), 2.34-2.43 (m, 1 H), 2.68-2.79 (m, 2 H), 3.16-3.25 (m, 2 H), 3.41-3.46 (m, 2 H), 3.88 (t, J = 6.5 Hz, 2 H), 4.03 (qd, J = 7.0, 2.5 Hz, 2 H) | E | m/z 354 (M + H)⁺ (ES⁺) at 7.33 min, UV active |
| 1-9 | Isomer 1 (racemic): Ethyl 4-{4-[N-(propan-2-yloxy)ethan-imidoyl]piperidin-1-yl}azepane-1-carboxylate | 1 and 25 | a | 400 MHz, (DMSO-d₆) δ: 1.13-1.19 (m, 9 H), 1.30-1.63 (m, 7 H), 1.71-1.89 (m, 6 H), 2.08-2.29 (m, 2 H), 2.34-2.45 (m, 1 H), 2.68-2.89 (m, 3 H), 3.16-3.24 (m, 2 H), 3.41-3.45 (m, 2 H), 4.03 (qd, J = 7.0, 2.5 Hz, 2 H), 4.10-4.19 (m, 1 H) | E | m/z 354 (M + H)⁺ (ES⁺) at 6.91 min, UV active |
| 1-9 | Isomer 2 (racemic): Ethyl 4-{4-[N-(propan-2-yloxy)ethan-imidoyl]piperidin-1-yl}azepane-1-carboxylate | 1 and 25 | a | 400 MHz, (DMSO-d₆) δ: 1.14-1.19 (m, 9 H), 1.29-1.86 (m, 13 H), 2.00-2.22 (m, 3 H), 2.34-2.44 (m, 1 H), 2.67-2.82 (m, 2 H), 3.16-3.25 (m, 2 H), 3.39-3.51 (m, 2 H), 4.03 (qd, J = 7.0, 2.5 Hz, 2 H), 4.12-4.21 (m, 1 H) | E | m/z 354 (M + H)⁺ (ES⁺) at 7.40 min, UV active |
| 1-10 | Isomer 1 (racemic): Ethyl 4-{4-[N-ethoxy-propanimidoyl]pipendin-1-yl}azepane-1-carboxylate | 3 and 23 | a | 400 MHz, (DMSO-d₆) δ: 0.99 (t, J = 7.5 Hz, 3 H), 1.14-1.19 (m, 6 H), 1.24-1.60 (m, 7 H), 1.71-1.86 (m, 3 H), 2.11-2.23 (m, 4 H), 2.34-2.41 (m, 1 H), 2.66-2.90 (m, 3 H), 3.13-3.27 (m, 2 H), 3.39-3.50 (m, 2 H), 3.94-4.05 (m, 4 H) | E | m/z 354 (M + H)⁺ (ES⁺) at 7.46 min, UV active |
| 1-10 | Isomer 2 (racemic): Ethyl 4-{4-[N-ethoxy-propanimidoyl]piperidin-1-yl}azepane-1-carboxylate | 3 and 23 | a | 400 MHz, (DMSO-d₆) δ: 0.98 (t, J = 7.5 Hz, 3 H), 1.14-1.19 (m, 6 H), 1.24-1.85 (m, 10 H), 2.00-2.21 (m, 5 H), 2.34-2.42 (m, 1 H), 2.68-2.82 (m, 2 H), 3.16-3.25 (m, 2 H), 3.39-3.51 (m, 2 H), 3.93-4.05 (m, 4 H) | E | m/z 354 (M + H)⁺ (ES⁺) at 7.63 min, UV active |
| 1-11 | Isomer 1 (racemic): Ethyl 4-{4-[N-propoxy-propanimidoyl]piperidin-1-yl}azepane-1-carboxylate | 3 and 24 | a | 400 MHz, (DMSO-d₆) δ: 0.87 (t, J = 7.5 Hz, 3 H), 0.99 (t, J = 7.5 Hz, 3 H), 1.15-1.19 (m, 3 H), 1.24-1.61 (m, 9 H), 1.70-1.86 (m, 3 H), 2.08-2.24 (m, 4 H), 2.33-2.44 (m, 1 H), 2.65-2.90 (m, 3 H), 3.14-3.27 (m, 2 H), 3.41-3.53 (m, 2 H), 3.88 (t, J = 6.5 Hz, 2 H), 4.0-4.05 (m, 2 H) | E | m/z 368 (M + H)⁺ (ES⁺) at 8.16 min, UV active |
| 1-11 | Isomer 2 (racemic): Ethyl 4-{4-[N-propoxy-propanimidoyl]piperidin-1-yl}azepane-1-carboxylate | 3 and 24 | a | 400 MHz, (DMSO-d₆) δ: 0.88 (t, J = 7.5 Hz, 3 H), 0.99 (t, J = 7.5 Hz, 3 H), 1.16-1.19 (m, 3 H), 1.24-1.90 (m, 12 H), 2.00-2.29 (m, 4 H), 2.34-2.43 (m, 1 H), 2.59-2.86 (m, 3 H), 3.16-3.25 (m, 2 H), 3.41-3.47 (m, 2 H), 3.87 (t, J = 6.5 Hz, 2 H), 3.99-4.14 (m, 2 H) | E | m/z 368 (M + H)⁺ (ES⁺) at 8.34 min, UV active |
| 1-12 | Isomer 1 (racemic): Ethyl 4-{4-[N-(propan-2-yloxy)propan-imidoyl]piperidin-1-yl}azepane-1-carboxylate | 3 and 25 | a | 400 MHz, (DMSO-d₆) δ: 0.99 (t, J = 7.5 Hz, 3 H), 1.14-1.83 (m, 20 H), 2.11-2.27 (m, 4 H), 2.34-2.42 (m, 1 H), 2.68-2.89 (m, 2 H), 3.17-3.27 (m, 2 H), 3.41-3.51 (m, 2 H), 4.03 (qd, J = 7.0, 2.0 Hz, 2 H), 4.12-4.22 (m, 1 H) | E | m/z 368 (M + H)⁺ (ES⁺) at 8.25 min, UV active |
| 1-12 | Isomer 2 (racemic): Ethyl 4-{4-[N-(propan-2-yloxy)propan-imidoyl]piperidin-1-yl}azepane-1-carboxylate | 3 and 25 | a | 400 MHz, (DMSO-d₆) δ: 0.98 (t, J = 7.5 Hz, 3 H), 1.14-1.92 (m, 19 H), 2.01-2.25 (m, 5 H), 2.32-2.46 (m, 1 H), 2.66-2.80 (m, 2 H), 3.16-3.25 (m, 2 H), 3.41-3.54 (m, 2 H), 4.03 (qd, J = 7.0, 2.0 Hz, 2 H), 4.11-4.20 (m, 1 H) | E | m/z 368 (M + H)⁺ (ES⁺) at 8.48 min, UV active |

TABLE 3-continued

| Ex. No. | Name | Intermediates | Synthetic method | $^1$H NMR | LCMS Method | LCMS data |
|---|---|---|---|---|---|---|
| 2-1 | Mixture of isomers 1: Ethyl 2-{4-[N-methoxy-ethanimidoyl]piperidin-1-yl}-6-azaspiro[3.4]octane-6-carboxylate | 16 | a | 400 MHz, (MeOD-d$_4$) δ: 1.25-1.30 (m, 3 H), 1.57-2.28 (m, 17 H), 2.82-3.11 (m, 4 H), 3.36-3.44 (m, 2 H), 3.78-3.80 (m, 3 H), 4.09-4.16 (m, 2 H) | D | m/z 338 (M + H)$^+$ (ES$^+$) at 6.22 min, UV active |
| 2-1 | Mixture of isomers 2: Ethyl 2-{4-[N-methoxy-ethanimidoyl]piperidin-1-yl}-6-azaspiro[3.4]octane-6-carboxylate | 16 | a | 400 MHz, (MeOD-d$_4$) δ: 1.27 (t, J = 7.0 Hz, 3 H), 1.61-1.71 (m, 2 H), 1.79-1.84 (m, 5 H), 1.93-2.06 (m, 7 H), 2.14-2.26 (m, 3 H), 2.78-3.08 (m, 3 H), 3.29 (s, 1 H), 3.41 (q, J = 7.0 Hz, 2 H), 3.80 (s, 3 H), 4.11 (q, J = 7.0 Hz, 2 H) | D | m/z 338 (M + H)$^+$ (ES$^+$) at 6.40 min, UV active |
| 2-2 | Isomer 1: Ethyl 2-{4-[N-methoxypropan-imidoyl]piperidin-1-yl}-6-azaspiro[3.4]octane-6-carboxylate | 18 | a | 400 MHz, (MeOD-d$_4$) δ: 1.11 (t, J = 7.5 Hz, 3 H), 1.25-1.30 (m, 3 H), 1.69-1.76 (m, 2 H), 1.87-1.99 (m, 8 H), 2.13-2.25 (m, 5 H), 2.81-3.07 (m, 3 H), 3.37-3.40 (m, 4 H), 3.79 (s, 3 H), 4.10-4.15 (m, 2 H) | D | m/z 352 (M + H)$^+$ (ES$^+$) at 6.72 min, UV active |
| 2-2 | Isomer 2: Ethyl 2-{4-[N-methoxypropan-imidoyl]piperidin-1-yl}-6-azaspiro[3.4]octane-6-carboxylate | 18 | a | 400 MHz, (MeOD-d$_4$) δ: 1.07 (t, J = 7.5 Hz, 3 H), 1.26-1.31 (m, 3 H), 1.65-2.33 (m, 15 H), 2.91-3.12 (m, 3 H), 3.36-3.41 (m, 4 H), 3.79 (s, 3 H), 4.13 (q, J = 7.0 Hz, 2 H) | D | m/z 352 (M + H)$^+$ (ES$^+$) at 6.82 min, UV active |
| 2-2 | Isomer 3: Ethyl 2-{4-[N-methoxypropan-imidoyl]piperidin-1-yl}-6-azaspiro[3.4]octane-6-carboxylate | 18 | a | 400 MHz, (MeOD-d$_4$) δ: 1.11 (t, J = 7.5 Hz, 3 H), 1.25-1.28 (m, 3 H), 1.65-1.71 (m, 2 H), 1.80-2.01 (m, 8 H), 2.06-2.32 (m, 5 H), 2.76-2.80 (m, 1 H), 2.96-3.01 (m, 2 H), 3.28-3.45 (m, 4 H), 3.79 (s, 3 H), 4.09-4.14 (m, 2 H) | D | m/z 352 (M + H)$^+$ (ES$^+$) at 6.91 min, UV active |
| 2-2 | Isomer 4: Ethyl 2-{4-[N-methoxypropan-imidoyl]piperidin-1-yl}-6-azaspiro[3.4]octane-6-carboxylate | 18 | a | 400 MHz, (MeOD-d$_4$) δ: 1.07 (t, J = 7.5 Hz, 3 H), 1.25-1.31 (m, 3 H), 1.61-2.32 (m, 15 H), 2.79-2.92 (m, 1 H), 2.99-3.01 (m, 2 H), 3.29-3.44 (m, 4 H), 3.79 (s, 3 H), 4.11 (q, J = 7.0 Hz, 2H) | D | m/z 352 (M + H)$^+$ (ES$^+$) at 7.01 min, UV active |
| 2-3 | Isomer 1: Ethyl 2-{4-[N-methoxybutan-imidoyl]piperidin-1-yl}-6-azaspiro[3.4]octane-6-carboxylate | 19 | a | 400 MHz, (MeOD-d$_4$) δ: 0.97 (t, J = 7.5 Hz, 3 H), 1.28 (td, J = 7.0, 2.5 Hz, 3 H), 1.54-1.63 (m, 3 H), 1.69-1.73 (m, 4 H), 1.84-1.95 (m, 6 H), 2.14-2.18 (m, 4 H), 2.74-2.87 (m, 1 H), 2.95-3.04 (m, 2 H), 3.35-3.40 (m, 4 H), 3.79 (s, 3 H), 4.13 (q, J = 7.0 Hz, 2 H) | D | m/z 366 (M + H)$^+$ (ES$^+$) at 7.42 min, UV active |
| 2-3 | Mixture of two isomers: Ethyl 2-{4-[N-methoxybutan-imidoyl]piperidin-1-yl}-6-azaspiro[3.4]octane-6-carboxylate | 19 | a | 400 MHz, (MeOD-d$_4$) δ: 0.91-0.99 (m, 3 H), 1.25-1.29 (m, 3 H), 1.48-1.98 (m, 12 H), 2.10-2.27 (m, 5 H), 2.74-2.84 (m, 1 H), 2.96-2.99 (m, 2 H), 3.28-3.43 (m, 4 H), 3.78 (m, 3 H), 4.09-4.15 (m, 2 H) | D | m/z 366 (M + H)$^+$ (ES$^+$) at 7.60 min, UV active |
| 2-3 | Isomer 4: Ethyl 2-{4-[N-methoxybutan-imidoyl]piperidin-1-yl}-6-azaspiro[3.4]octane-6-carboxylate | 19 | a | 400 MHz, (MeOD-d$_4$) δ: 0.95 (t, J = 7.5 Hz, 3 H), 1.27 (t, J = 7.0 Hz, 3 H), 1.48-1.58 (m, 2 H), 1.64-1.73 (m, 3 H), 1.85-1.89 (m, 2 H), 1.94-2.28 (m, 10 H), 2.92-3.18 (m, 3 H), 3.31 (s, 2 H), 3.42 (q, J = 7.0 Hz, 2 H), 3.78 (s, 3 H), 4.12 (q, J = 7.0 Hz, 2 H) | D | m/z 366 (M + H)$^+$ (ES$^+$) at 7.70 min, UV active |
| 3-1 | Mixture of isomers: Ethyl 4-{4-[N'-methoxy-N-(2-methylpropyl)carbam-imidoyl]piperidin-1-yl}azepane-1-carboxylate | 21 | b | 400 MHz, (DMSO-d$_6$) δ: 0.85 (d, J = 6.5 Hz, 6 H), 1.16-1.24 (m, 8 H), 1.35-2.06 (m, 11 H), 2.83 (t, J = 6.5 Hz, 2 H), 3.18-3.30 (m, 2 H), 3.43-3.51 (m, 3 H), 3.59 (s, 3 H), 4.02-4.06 (m, 2 H), 5.42 (s, 1 H) | C | m/z 383 (M + H)$^+$ (ES$^+$) at 1.78 min, UV active |
| 4-1 | Mixture of isomers: Ethyl 4-(4-{cyano[(propan-2-yloxy)imino]methyl}piperidin-1-yl)azepane-1-carboxylate | 21 | c | 400 MHz, (DMSO-d$_6$) δ: 1.17 (td, J = 7.0, 1.5 Hz, 3 H), 1.25 (d, J = 6.5 Hz, 6 H), 1.35-1.81 (m, 10 H), 2.15-2.47 (m, 4 H), 2.71-2.83 (m, 2 H), 3.16-3.25 (m, 2 H), 3.38-3.49 (m, 2 H), 4.03 (qd, J = 7.0, 1.5 Hz, 2 H), 4.42-4.53 (m, 1 H) | B | m/z 365 (M + H)$^+$ (ES$^+$) at 4.70 min, UV active |

BIOLOGICAL ACTIVITY

Example A

Phospho-ERK1/2 Assays

Functional assays were performed using the Alphascreen Surefire phospho-ERK1/2 assay (Crouch & Osmond, *Comb. Chem. High Throughput Screen,* 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader.

$pEC_{50}$ and $E_{max}$ figures were calculated from the resulting data for each receptor subtype.

For all examples cis and trans oxime isomers exist and have been separated, unless stated otherwise, absolute configuration has not been defined and assignment of different isomers based on their retention time on LCMS analytical trace has been performed. When racemic starting materials are used then the separated isomers are still racemic mixtures. For some examples two additional diastereomers exist across the cyclobutane ring; when possible these have been separated, unless stated otherwise, and assigned based on their retention time on LCMS analytical trace. Analytical data for active isomers is reported in Table 3. Data for several weakly active compounds are also included in Table 4 to highlight a preference of absolute stereochemistry.

The results are set out in Table 4 below.

TABLE 4

| | Muscarinic Activity | | | |
|---|---|---|---|---|
| Ex. No. | $pEC_{50}$ $M_1$ (% Emax cf. ACh) | $pEC_{50}$ $M_2$ (% Emax cf. ACh) | $pEC_{50}$ $M_3$ (% Emax cf. ACh) | $pEC_{50}$ $M_4$ (% Emax cf. ACh) |
| ACh | 8.3 (102) | 7.8 (105) | 8.1 (115) | 8.1 (110) |
| 1-1 Isomer 2 (racemic) | 5.8 (54) | <4.7 (4) | <4.7 (1) | 6.9 (71) |
| (S)-1-1 Isomer 1 | 6.2 (47) | NT | NT | 6.7 (31) |
| (S)-1-1 Isomer 2 | 6.3 (49) | <4.7 (7) | <4.7 (0) | 6.7 (62) |
| 1-2 Isomer 1 (racemic) | 6.3 (58) | <4.7 (2) | <4.7 (37) | 7.1 (99) |
| 1-2 Isomer 2 (racemic) | 6.4 (83) | <4.7 (7) | <4.7 (1) | 7.6 (94) |
| (S)-1-2 Isomer 1 | <4.7 (21) | <4.7 (11) | <4.7 (9) | 7.2 (81) |
| (S)-1-2 Isomer 2 | 6.3 (36) | <4.7 (5) | <4.7 (7) | 7.3 (81) |
| 1-3 Isomer 1 (racemic) | 6.5 (106) | NT | NT | 7.6 (85) |
| 1-3 Isomer 2 (racemic) | 7.2 (92) | <4.7 (21) | <4.7 (17) | 7.3 (83) |
| (S)-1-3 Isomer 2 | 6.6 (93) | <4.7 (7) | <4.7 (0) | 7.6 (126) |
| 1-4 Isomer 1 (racemic) | 6.4 (87) | <4.7 (24) | <4.7 (5) | 7.3 (115) |
| 1-4 Isomer 2 (racemic) | 6.5 (95) | <4.8 (7) | <4.8 (6) | 7.5 (107) |
| 1-5 Isomer 2 (racemic) | 6.5 (105) | <4.7 (22) | <4.7 (4) | 7.5 (104) |
| 1-6 Isomer 2 (racemic) | 7.4 (96) | <4.7 (10) | <4.7 (16) | 6.9 (65) |
| 1-7 Isomer 1 (racemic) | 6.2 (48) | NT | NT | 6.2 (52) |
| 1-7 Isomer 2 (racemic) | 6.3 (66) | NT | NT | 6.6 (62) |
| 1-8 Isomer 1 (racemic) | 6.1 (65) | NT | NT | 6.1 (46) |
| 1-8 Isomer 2 (racemic) | 6.5 (85) | NT | NT | 6.5 (50) |
| 1-9 Isomer 1 (racemic) | 6.2 (57) | NT | NT | <4.7 (0) |
| 1-9 Isomer 2 (racemic) | 6.2 (46) | NT | NT | 6.4 (81) |
| 1-10 Isomer 1 (racemic) | 6.3 (58) | NT | NT | 7.0 (89) |
| 1-11 Isomer 1 (racemic) | 6.6 (107) | NT | NT | 6.9 (72) |
| 1-11 Isomer 2 (racemic) | 6.8 (99) | <4.7 (19) | <4.7 (6) | 7.2 (97) |
| 1-12 Isomer 1 (racemic) | 7.0 (98) | <4.7 (5) | <4.7 (6) | 7.2 (80) |
| 1-12 Isomer 2 (racemic) | 6.5 (72) | <4.7 (2) | <4.7 (1) | 7.6 (101) |
| 2-1 Mixture of isomers 2 | 6.7 (89) | <4.7 (71) | <4.7 (9) | 7.2 (68) |
| 2-2 Isomer 3 | <4.7 (5) | <4.7 (7) | <4.7 (2) | 7.3 (67) |
| 2-2 Isomer 4 | 6.7 (59) | <4.7 (69) | <4.7 (18) | 7.7 (105) |
| 2-3 Mixture of two isomers | <4.7 (22) | <4.7 (7) | <4.7 (5) | 7.7 (93) |
| 2-3 Isomer 4 | 6.8 (87) | <4.7 (15) | <4.7 (7) | 7.6 (77) |
| 3-1 Mixture of isomers | 6.6 (136) | NT | NT | 6.4 (56) |
| 4-1 Mixture of isomers | 7.0 (109) | <4.7 (4) | <4.7 (5) | 7.1 (72) |

Example B

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and optionally 1% by weight of magnesium stearate and filling the resulting mixture into standard opaque hard gelatin capsules.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1):

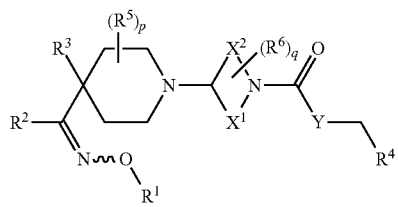

or a salt thereof, wherein:
p is 0, 1 or 2;
q is 0, 1 or 2;
Y is N, O, S or C;
$X^1$ and $X^2$ are saturated hydrocarbon groups which together contain a total of four to nine carbon atoms and which link together such that the moiety:

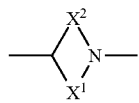

forms a mono or bicyclic ring system;
$R^1$ is a $C_{1-6}$ non-aromatic hydrocarbon group which is optionally substituted with one to six fluorine atoms and wherein one or two, but not all, carbon atoms of the hydrocarbon group are optionally replaced by a heteroatom selected from O, N and S and oxidised forms thereof;
$R^2$ is cyano or a $C_{1-6}$ non-aromatic hydrocarbon group which is optionally substituted with one to six fluorine atoms and wherein one or two, but not all, carbon atoms of the hydrocarbon group are optionally replaced by a heteroatom selected from O, N and S and oxidised forms thereof;
$R^3$ is selected from hydrogen; halogen; cyano; hydroxy; $C_{1-3}$ alkoxy; and a $C_{1-5}$ non-aromatic hydrocarbon group which is optionally substituted with one to six fluorine atoms and wherein one or two, but not all, carbon atoms of the hydrocarbon group are optionally replaced by a heteroatom selected from O, N and S and oxidized forms thereof;
$R^4$ is H or a $C_{1-6}$ non-aromatic hydrocarbon group which is optionally substituted with one to six fluorine atoms and wherein one or two, but not all, carbon atoms of the hydrocarbon group are optionally replaced by a heteroatom selected from O, N and S and oxidised forms thereof;
$R^5$ is fluorine; and
$R^6$ is fluorine.

2. The compound according to claim 1 wherein $R^1$ is selected from methyl, ethyl, propyl or isopropyl.

3. The compound according to claim 1 wherein $R^2$ is selected from cyano, methyl, ethyl, propyl, isopropyl, butyl or isobutyl.

4. The compound according to claim 1 wherein $R^3$ is selected from hydrogen, fluorine and methoxy.

5. The compound according to claim 1 wherein $R^4$ is selected from hydrogen, methyl, ethyl, ethynyl and 1-propynyl.

6. The compound according to claim 1 wherein p is 0.

7. The compound according to claim 1 wherein q is 0.

8. The compound according to claim 1 wherein the bicyclic ring system formed by the moiety:

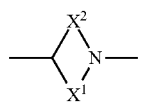

is selected from:
(a) piperidine;
(b) azepane;
(c) an azabicyclo-octane or azabicyclo-nonane ring system;
(d) a 2-aza-spiro[3.4]octane or a 6-aza-spiro[3.4]octane ring system; and
(e) a cyclopentanopyrrolidine ring system.

9. The compound according to claim 8 wherein the bicyclic ring system formed by the moiety:

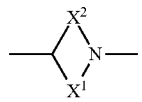

is selected from ring systems below:

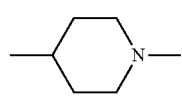
A

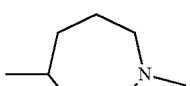
B

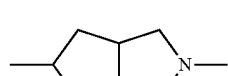
C

D

E

F

-continued

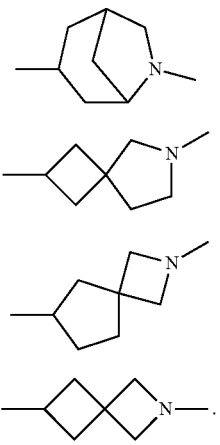

G

H

I

J

10. The compound according to claim 1 having the formula (2):

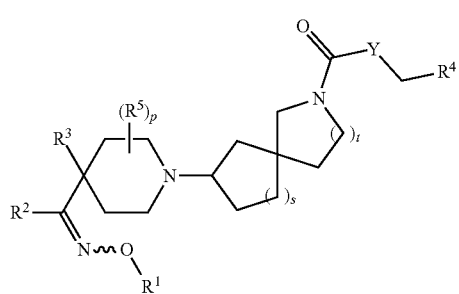

(2)

wherein s is 0 or 1 and t is 0 or 1.

11. The compound according to claim 1 which is selected from the group consisting of:
Ethyl 4-{4-[N-methoxyethanimidoyl]piperidin-1-yl} azepane-1-carboxylate;
Ethyl (4S)-4-{4-[N-methoxyethanimidoyl]piperidin-1-yl} azepane-1-carboxylate;
Ethyl 4-{4-[N-methoxypropanimidoyl]piperidin-1-yl} azepane-1-carboxylate;
Ethyl (4S)-4-{4-[N-methoxypropanimidoyl]piperidin-1-yl} azepane-1-carboxylate;
Ethyl 4-{4-[N-methoxybutanimidoyl]piperidin-1-yl} azepane-1-carboxylate;
Ethyl (4S)-4-{4-[N-methoxybutanimidoyl]piperidin-1-yl} azepane-1-carboxylate;
Ethyl 4-{4-[N-methoxy-2-methylpropanimidoyl]piperidin-1-yl} azepane-1-carboxylate;
Ethyl 4-{4-[N-methoxy-2-methylpropanimidoyl]piperidin-1-yl} azepane-1-carboxylate;
Ethyl 4-{4-[N-methoxy-4-methylpentanimidoyl]piperidin-1-yl} azepane-1-carboxylate;
Ethyl 4-{4-[N-ethoxyethanimidoyl]piperidin-1-yl} azepane-1-carboxylate;
Ethyl 4-{4-[N-propoxyethanimidoyl]piperidin-1-yl} azepane-1-carboxylate;
Ethyl 4-14-[N-(propan-2-yloxy)ethanimidoyl]piperidin-1-yl} azepane-1-carboxylate;
Ethyl 4-{4-[N-ethoxypropanimidoyl]piperidin-1-yl} azepane-1-carboxylate;
Ethyl 4-{4-[N-propoxypropanimidoyl]piperidin-1-yl} azepane-1-carboxylate;
Ethyl 4-{4-[N-(propan-2-yloxy)propanimidoyl]piperidin-1-yl} azepane-1-carboxylate;
Ethyl 2-{4-[N-methoxyethanimidoyl]piperidin-1-yl}-6-azaspiro [3.4] octane-6-carboxylate;
Ethyl 2-{4-[N-methoxypropanimidoyl]piperidin-1-yl}-6-azaspiro [3.4] octane-6-carboxylate;
Ethyl 2-{4-[N-methoxybutanimidoyl]piperidin-1-yl}-6-azaspiro [3.4] octane-6-carboxylate;
Ethyl 4-{4-[N'-methoxy-N-(2-methylpropyl)carbamimidoyl]piperidin-1-yl} azepane-1-carboxylate; and
Ethyl 4-(4-1 cyano [(propan-2-yloxy)imino] methyl}piperidin-1-yl)azepane-1-carboxylate.

12. The compound according to claim 1 which is selected from the group consisting of:
Ethyl 4-{4-[N-methoxy propanimidoyl]piperidin-1-yl} azepane-1-carboxylate;
Ethyl 4-{4-[N-methoxybutanimidoyl]piperidin-1-yl} azepane-1-carboxylate;
Ethyl 4-{4-[N-methoxy-2-methylpropanimidoyl]piperidin-1-yl} azepane-1-carboxylate;
Ethyl 4-{4-[N-methoxy-2-methylpropanimidoyl]piperidin-1-yl} azepane-1-carboxylate;
Ethyl 4-{4-[N-(propan-2-yloxy)propanimidoyl]piperidin-1-yl} azepane-1-carboxylate;
Ethyl 2-{4-[N-methoxypropanimidoyl]piperidin-1-yl}-6-azaspiro [3.4] octane-6-carboxylate; and
Ethyl 2-{4-[N-methoxybutanimidoyl]piperidin-1-yl}-6-azaspiro [3.4] octane-6-carboxylate.

13. A pharmaceutical composition comprising the compound as defined in claim 1 and a pharmaceutically acceptable excipient.

14. The compound according to claim 1 having muscarinic $M_1$ receptor and/or $M_4$ receptor agonist activity.

15. A method of treating a subject suffering from Alzheimer's Disease, an acute, chronic, neuropathic, or inflammatory pain, comprising administering to the subject an effective amount of the compound according to claim 1 that exhibits selectivity for the $M_1$ and $M_4$ receptor relative to the $M_2$ and $M_3$ receptor subtypes.

16. A method of treating a subject suffering from schizophrenia, comprising administering to the subject an effective amount of the compound according to claim 1 that exhibits selectivity for the $M_4$ receptor relative to the $M_1$, $M_2$ and $M_3$ receptor subtypes.

* * * * *

UNITED STATES PATENT AND TRADEMARK OFFICE
CERTIFICATE OF CORRECTION

| | | |
|---|---|---|
| PATENT NO. | : 11,208,396 B2 | Page 1 of 1 |
| APPLICATION NO. | : 15/772785 | |
| DATED | : December 28, 2021 | |
| INVENTOR(S) | : Brown et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 589 days.

Signed and Sealed this
Twenty-ninth Day of November, 2022

Katherine Kelly Vidal
*Director of the United States Patent and Trademark Office*